(12) United States Patent
Song et al.

(10) Patent No.: US 8,147,814 B2
(45) Date of Patent: *Apr. 3, 2012

(54) PERSONAL CARE COMPOSITIONS COMPRISING CERTAIN DYE-POLYMER COMPLEXES

(75) Inventors: Zhiqiang Song, Newtown, CT (US); Bingham Scott Jaynes, New City, NY (US); Joseph Anthony Lupia, Monroe, NY (US); Xian-Zhi Zhou, Leonia, NJ (US)

(73) Assignee: BASF SE, Ludwigshafen (DE)

( * ) Notice: Subject to any disclaimer, the term of this patent is extended or adjusted under 35 U.S.C. 154(b) by 17 days.

This patent is subject to a terminal disclaimer.

(21) Appl. No.: 12/231,579

(22) Filed: Sep. 4, 2008

(65) Prior Publication Data

US 2009/0060849 A1 Mar. 5, 2009

Related U.S. Application Data

(60) Provisional application No. 60/967,534, filed on Sep. 5, 2007.

(51) Int. Cl.
| | |
|---|---|
| A61K 8/73 | (2006.01) |
| A61K 8/00 | (2006.01) |
| A61K 8/18 | (2006.01) |
| A61K 8/72 | (2006.01) |
| A61K 8/81 | (2006.01) |
| A61K 8/92 | (2006.01) |
| A61Q 11/00 | (2006.01) |
| A61Q 17/04 | (2006.01) |
| A61Q 3/00 | (2006.01) |
| A61Q 1/02 | (2006.01) |
| A61Q 19/04 | (2006.01) |
| A61Q 15/00 | (2006.01) |
| A61Q 1/00 | (2006.01) |
| A61Q 1/12 | (2006.01) |
| A61Q 5/00 | (2006.01) |
| A61Q 7/00 | (2006.01) |
| A61Q 1/10 | (2006.01) |
| A61Q 5/02 | (2006.01) |
| A61Q 1/14 | (2006.01) |
| A61Q 19/00 | (2006.01) |
| A61Q 19/10 | (2006.01) |
| C11D 3/00 | (2006.01) |

(52) U.S. Cl. ......... 424/70.17; 424/49; 424/54; 424/59; 424/61; 424/63; 424/65; 424/69; 424/70.1; 424/70.11; 424/70.6; 424/70.7; 510/119; 510/123; 510/130; 510/504; 8/405

(58) Field of Classification Search .............. 8/137, 405; 510/119, 130, 123, 504; 424/49, 70.7, 54, 424/59, 61, 63, 65, 69, 70.1, 70.11, 70.6, 424/70.17

See application file for complete search history.

(56) References Cited

U.S. PATENT DOCUMENTS

| | | | | |
|---|---|---|---|---|
| 4,213,960 | A * | 7/1980 | Grollier et al. | 424/47 |
| 4,492,686 | A | 1/1985 | Guillon et al. | 424/61 |
| 4,820,509 | A * | 4/1989 | Yamazaki et al. | 424/61 |
| 5,100,951 | A * | 3/1992 | Fillipo et al. | 524/501 |
| 5,703,033 | A * | 12/1997 | Sherry et al. | 510/237 |
| 5,912,221 | A * | 6/1999 | Van Leeuwen et al. | 510/360 |
| 6,001,899 | A * | 12/1999 | Gundlach et al. | 523/160 |
| 6,005,022 | A * | 12/1999 | Schwarz, Jr. | 523/160 |
| 6,281,187 | B1* | 8/2001 | Smerznak | 510/418 |
| 6,833,336 | B2* | 12/2004 | Panandiker et al. | 442/121 |
| 7,012,053 | B1* | 3/2006 | Barnabas et al. | 510/287 |
| 2004/0147630 | A1* | 7/2004 | Schmid et al. | 523/160 |
| 2004/0182533 | A1* | 9/2004 | Blum et al. | 162/135 |
| 2004/0229991 | A1* | 11/2004 | SenGupta et al. | 524/445 |
| 2004/0231070 | A1* | 11/2004 | Morrissey et al. | 8/405 |
| 2005/0043200 | A1* | 2/2005 | Barry et al. | 510/421 |
| 2006/0110344 | A1* | 5/2006 | Hata et al. | 424/63 |
| 2006/0111264 | A1* | 5/2006 | Smets et al. | 510/475 |
| 2006/0287216 | A1 | 12/2006 | Song | 510/499 |
| 2007/0259800 | A1* | 11/2007 | Boutique et al. | 510/276 |
| 2008/0274071 | A1* | 11/2008 | Kaplan et al. | 424/70.11 |
| 2009/0025601 | A1* | 1/2009 | Vasudevan et al. | 106/31.65 |

FOREIGN PATENT DOCUMENTS

| | | | |
|---|---|---|---|
| EP | 1852496 | * | 7/2007 |
| WO | 00/22077 | | 4/2000 |
| WO | 00/25730 | | 5/2000 |
| WO | 00/25731 | | 5/2000 |
| WO | WO 2007073857 A1 | * | 7/2007 |

OTHER PUBLICATIONS

Qian Zhang, et al., Chem. Mater. 2008, 20, 29-31.
Nalco Product Bulletin, MERQUAT, Polyquaternium 6 Series.

* cited by examiner

*Primary Examiner* — Lorna M Douyon
*Assistant Examiner* — Tanisha Diggs
(74) *Attorney, Agent, or Firm* — Shiela A. Loggins; Tyler A. Stevenson

(57) ABSTRACT

The present invention relates to personal care compositions comprising certain dye-polymer complexes. Additionally, methods for coloration of personal care compositions using said dye-polymer complexes are disclosed.

23 Claims, No Drawings

PERSONAL CARE COMPOSITIONS COMPRISING CERTAIN DYE-POLYMER COMPLEXES

This application claims benefit of U.S. provisional application No. 60/967,534, filed Sep. 5, 2007, the disclosure of which is incorporated by reference.

The present invention relates to personal care compositions comprising certain dye-polymer complexes. Additionally, methods for the coloration of personal care compositions using said dye-polymer complexes are disclosed.

BACKGROUND OF THE INVENTION

WO 00/25730 and WO 00/25731 are aimed at the stabilization of body care and household products.

U.S. Pat. app. No. 60/377,381, filed May 2, 2002, discloses the use of selected hindered nitroxyl, hydroxylamine and hydroxylamine salt compounds in formulations of body care products, household products, textiles and fabrics, and is incorporated herein by reference.

U.S. Pat. No. 4,492,686 discloses cosmetic makeup compositions containing pigments salified with amine functions, and is incorporated herein by reference.

It is now found that certain dye-polymer complexes provide outstanding stable coloration of personal care compositions and products.

DETAILED DESCRIPTION

The present invention pertains to a personal care composition comprising
(a) an effective colorizing amount of one or more dye-polymer complexes formed from
  (i) one or more cationic polymers and
  (ii) one or more anionic dyes,
wherein components (a) (i) and (a) (ii) are complexed to form particles prior to addition to said personal care composition and wherein said complex remains as particles in the finished product; and
(b) a cosmetically acceptable adjuvant,
with the proviso that the cationic polymer of component (a) (i) is not a polyvinylamine hydrochloride homopolymer or is not a homopolymer of polydiallyldimethylammonium chloride with a molecular weight of less than 50,000 Daltons.

The cationic polymers of component (a) (i) can be natural, modified natural polymers or synthetic polymers. Examples of natural and modified natural cationic polymers are chitosan (and salts) and cationic starch.

Suitable cationic polymers of component (a) (i) for use in the present invention contain cationic nitrogen-containing moieties such as quaternary ammonium or cationic protonated amino moieties. The cationic protonated amines can be primary, secondary, or tertiary amines (preferably secondary or tertiary), depending upon the particular species and the selected pH of the personal care composition. The cationic polymers also have a cationic charge density ranging from about 0.2 meq/gm to about 13 meq/gm, preferably at least about 0.4 meq/gm, more preferably at least about 0.6 meq/gm., at the pH of intended use of the personal care composition, which pH will generally range from about pH 4 to about pH 9, preferably between about pH 5 and about pH 8.

The cationic nitrogen containing moiety of the cationic polymer is generally present as a substituent on all, or more typically on some, of the monomer units thereof. The cationic polymer of component (a) (i) for use in the dye-polymer complexes of the instant invention includes homopolymers, copolymers, terpolymers, and so forth, of quaternary ammonium or cationic amine-substituted monomer units, optionally in combination with non-cationic monomers. Non limiting examples of such polymers are described in the CTFA Cosmetic Ingredient dictionary, $3^{rd}$ edition, edited by Estrin, Crosley, and Haynes, (The Cosmetics, Toiletry, and Fragrance Association, Inc. Washington, D.C. (1982)), which is incorporated by reference.

Suitable cationic polymers as component (a) (i) for the dye-polymer complex of the present invention include, but are not limited to, polymers containing more than 2, preferably more than 100, and more preferably more than 1000, ionizable or quaternizable cationic groups which include, but are not limited to, primary, secondary, tertiary amines and their salts, and quaternary ammonium and phosphonium salts, and the like.

Cationic polymers of component (a) (i) may contain a Mannich base, polyamine, polyethyleneimine, polyamidoamine/epichlorohydrins, polyamine epichlorohydrin products, dicyandiamide polymers including polyamine-dicyandiamide and polydicyandiamide formaldehyde polymers. Additional examples might be polyamine-epihalohydrin resins, such as polyaminopolyamide-epihalohydrin resins which are cationic thermosetting materials used to increase the wet strength of papers. Additionally, non-crosslinked reaction products of epichlorohydrin and amines, such as dimethylamine are cationic polymers of component (a) (i). Additionally, crosslinked reaction products of epichlorohydrin and amines, such as dimethylamine with ethylenediamine as a crosslinking agent are cationic polymers of component (a) (i). These polymers may be linear or crosslinked.

According to the instant invention, synthetic cationic polymers of component (a) (i) can be polymers obtained from homopolymerization of at least one cationic monomer $I_b$ or copolymerization of $I_b$ with a copolymerizable monomer II. Suitable cationic monomers $I_b$ include, but are not limited to, diallyldimethyl ammonium chloride (DADMAC), diallyldimethyl ammonium bromide, diallyidimethyl ammonium sulfate, diallyldimethyl ammonium phosphates, dimethallyldimethyl ammonium chloride, diethylallyl dimethyl ammonium chloride, diallyl di(beta-hydroxyethyl) ammonium chloride, and diallyl di(beta-ethoxyethyl) ammonium chloride, aminoalkyl acrylates such as dimethylaminoethyl acrylate, diethylaminoethyl acrylate, and 7-amino-3,7-dimethyloctyl acrylate, and their salts including their alkyl and benzyl quaternized salts; N,N'-dimethylaminopropyl acrylamide and its salts, allylamine and its salts, methyldiallylamine and its salts, diallylamine and its salts, methylallylamine and its salts, dimethylallylamine and its salts, vinylamine (obtained by hydrolysis of vinyl alkylamide polymers) and its salts, vinyl pyridine and its salts, and mixtures thereof.

Representative examples is selected from the group consisting of suitable cationically charged or potentially cationically charged monomers $I_b$ including dimethylaminoethyl acrylate methyl chloride quaternary salt, dimethylaminoethyl acrylate methyl sulfate quaternary salt, dimethyaminoethyl acrylate benzyl chloride quaternary salt, dimethylaminoethyl acrylate sulfuric acid salt, dimethylaminoethyl acrylate hydrochloric acid salt, dimethylaminoethyl methacrylate methyl chloride quaternary salt, dimethylaminoethyl methacrylate methyl sulfate quaternary salt, dimethylaminoethyl methacrylate benzyl chloride quaternary salt, dimethylaminoethyl methacrylate sulfuric acid salt, dimethylaminoethyl methacrylate hydrochloric acid salt, diethylaminoethyl acrylate, diethylaminoethyl acrylate methyl chloride quaternary salt, diethylaminoethyl methacrylate, diethylaminoethyl methacrylate methyl chloride quaternary salt, methacrylamidopropyltrimethylammonium chloride, acrylamidopropyltrimethylammonium chloride, dimethylaminopropylacrylamide methyl sulfate quaternary salt, dimethylaminopropylacrylamide sulfuric acid salt, dimethylaminopropylacrylamide hydrochloric acid salt, diallyldiethylammonium chloride, diallyldimethyl ammonium chloride, diallylamine, and vinylpyridine.

Further specific examples of cationic monomers or potentially cationic monomers $I_b$ are 2-vinyl-N-methylpyridinium chloride, (p-vinylphenyl)-trimethylammonium chloride, 1-methacryloyl-4-methyl piperazine, Mannich poly acrylamides i.e. polyacrylamide reacted with dimethyl amine formaldehyde adduct to give the N-(dimethyl amino methyl) and (meth)acrylamido propyltrimethyl ammonium chloride.

According to the instant invention, cationic polymers of component (a) (i) also include the polymers formed from polyfunctional epoxides, for example, di-epoxy or di-glycidyl compounds and polyfunctional amines. The cationic polymers from step polymerization may also include those known as "ionenes" formed by reacting difunctional alkylhalide (e.g., 1,6-dibromohexane) and polyfunctional amines, for example, ethylenediamine.

For purposes of the instant invention, potentially cationic monomers $I_b$ may be for example monomers that give a cationic charge under acidic conditions such as when an amine functionality on the potentially cationic monomer is protonated.

Monomers containing tertiary amine groups $I_b$ may also be converted into quaternary ammonium groups by reaction with quarternizing agents to produce a cationic polymer. There are no particular limitations on the quaternizing agents that can be used to quaternize the tertiary amino groups on the polymer or monomer. For example, the quaternizing agents may include alkyl halides such as methyl chloride, ethyl chloride, methyl bromide, ethyl bromide, methyl iodide, ethyl iodide and long chain alkyl halides such as $C_6$-$C_{24}$ alkyl halides; alkyl halide carboxylates such as sodium chloroacetate, sodium bromoacetate, and sodium iodoacetate, benzyl halides such as benzyl chloride, benzyl bromide and benzyl iodidie, sulfonic acid ester derivatives such as dimethyl sulfate, diethyl sulfate, methyl o-toluene sulfonate, methyl p-toluene sulfonate, ethyl o-toluene sulfonate, ethyl p-toluene sulfonate, methyl methane sulfonate, ethyl methane sulfonate, methyl benzene sulfonate and ethyl benzene sulfonate. Moreover, polyacrylamide can be rendered partially cationic by reaction with glycidyl dimethyl ammonium chloride.

The most preferred cationic monomers are DADMAC and dimethylaminoethyl acrylate and its salts, including its alkyl and benzyl quaternized salts. Suitable water-soluble cationic polymers are reaction products of 0.1 to 100 weight percent, preferably 10 to 100 weight percent, and most preferably 50 to 100 weight percent, of at least one cationic monomer $I_b$, preferably 0 to 90 weight percent, and most preferably 0 to 50 weight percent, of one or more other copolymerizable monomers II, and optionally, 0 to 10 weight percent of a crosslinking agent III.

Copolymerizable monomers II suitable for use with cationic monomers $I_b$ such as DADMAC for the cationic polymer include, without limitation, selected vinyl and (meth)acrylate-based compounds, other unsaturated compounds such as styrene, (meth)acrylonitrile and esters of unsaturated polyfunctional acids.

Examples of suitable vinyl compounds for monomer II include, but are not limited to, styrene; vinyl esters of $C_2$ to $C_{18}$ carboxylic acids, such as vinyl acetate and vinyl butyrate; N-vinyl amides of $C_2$ to $C_{18}$ carboxylic acids, such as N-vinyl acetamide, and the like.

The (meth)acrylate based compounds suitable as monomer II include, but are not limited to, esters of (meth)acrylic acid, amides of (meth)acrylic acid, esters of acrylic acid and amides of acrylic acid.

Esters of (meth)acrylic acid or (meth)acrylates or and esters of acrylic acid and amides of acrylic acid encompass: long- and short-chain alkyl (meth)acrylates such as methyl (meth)acrylate, ethyl (meth)acrylate, propyl (meth)acrylate, isopropyl (meth)acrylate, butyl (meth)acrylate, amyl (meth)acrylate, isobutyl (meth)acrylate, t-butyl (meth) acrylate, pentyl (meth)acrylate, isoamyl (meth)acrylate, hexyl (meth)acrylate, heptyl (meth)acrylate, octyl (meth) acrylate, isooctyl (meth)acrylate, 2-ethylhexyl (meth) acrylate, nonyl (meth)acrylate, decyl (meth)acrylate, isodecyl (meth)acrylate, undecyl (meth)acrylate, dodecyl (meth)acrylate, lauryl (meth)acrylate, octadecyl (meth) acrylate, and stearyl (meth)acrylate; alkoxyalkyl (meth) acrylates, particularly $C_1$-$C_4$alkoxy $C_1$-$C_4$alkyl (meth) acrylates such as butoxyethyl acrylate and ethoxyethoxyethyl acrylate; aryloxyalkyl (meth)acrylates, particularly aryloxy $C_1$-$C_4$alkyl (meth)acrylates, such as phenoxyethyl acrylate (e.g., Ageflex, Ciba Specialty Chemicals) monocyclic and polycyclic aromatic or non-aromatic acrylates such as cyclohexyl acrylate, benzyl acrylate, dicyclopentadienyl acrylate, dicyclopentanyl acrylate, tricyclodecanyl acrylate, bornyl acrylate, isobornyl acrylate (e.g. Ageflex IBOA, Ciba Specialty Chemicals), tetrahydrofurfuryl acrylate (e.g. SR285, Sartomer Company, Inc.), caprolactone acrylate (e.g. SR495, Sartomer Company, Inc.), and acryloylmorpholine; alcohol-based (meth)acrylates such as polyethylene glycol monoacrylate, polypropylene glycol monoacrylate, methoxyethylene glycol acrylate, methoxypolypropylene glycol acrylate, methoxypolyethylene glycol acrylate, ethoxydiethylene glycol acrylate, and various alkoxylated alkylphenol acrylates such as ethoxylated(4) nonylphenol acrylate (e.g. Photomer 4003, Henkel Corp.);

amides of (meth)acrylic acid such as diacetone acrylamide, isobutoxymethyl acrylamide, and t-octyl acrylamide; and esters of polyfunctional unsaturated acids such as maleic acid ester and fumaric acid ester.

With respect to the long and short chain alkyl acrylates listed above, a short chain alkyl acrylate is one having an alkyl group with 6 or less carbons and a long chain alkyl acrylate is one having an alkyl group with 7 or more carbons.

Suitable monomers are either commercially available or readily synthesized using reaction schemes known in the art. For example, most of the above-listed acrylate monomers can be synthesized by reacting an appropriate alcohol or amide with an acrylic acid or acryloyl chloride.

Specific examples of preferred compounds for use as other copolymerizable monomers II are exemplified by formula IV:

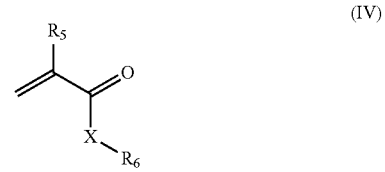

(IV)

wherein
R$_5$ is H or CH$_3$,
X is a divalent radical —O—, —NR$_7$—, or —NH—;

$R_6$ is $C_1$-$C_{12}$alkyl, $C_1$-$C_{12}$alkoxy, phenyl$C_1$-$C_6$alkylene, wherein the phenyl radical may be unsubstituted or substituted one to three times by $C_1$-$C_{12}$alkyl or $C_1$-$C_{12}$alkoxy, and the $C_1$-$C_6$alkylene group may be interrupted one or more times by oxygen.

Particularly preferred other copolymerizable monomers II are exemplified by:

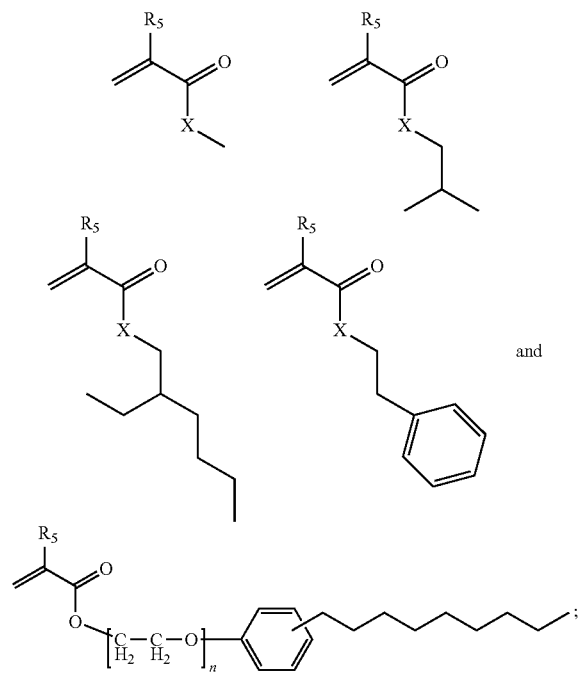

and wherein $R_5$ and X are as defined above and n is a number from 1 to 5, preferably 2 or 3.

Suitable crosslinking agents III can be polyfunctional ethylenically unsaturated monomers which include, without limitation, alkoxylated bisphenol A diacrylates such as ethoxylated bisphenol A diacrylate with ethoxylation being 2 or greater, preferably ranging from 2 to about 30 (e.g. SR349 and SR601 available from Sartomer Company, Inc. West Chester, Pa. and Photomer 4025 and Photomer 4028, available from Henkel Corp., Ambler, Pa.), and propoxylated bisphenol A diacrylate with propoxylation being 2 or greater, preferably ranging from 2 to about 30.

Preferred examples of suitable crosslinking agents III include methylene bisacrylamide, pentaerythritol, di-, tri- and tetra-acrylate, divinylbenzene, polyethylene glycol diacrylate and bisphenol A diacrylate.

According to the instant invention, if a cationic copolymer of component (a) (i) is present, then the weight ratio of monomer Ib to monomer II is from about 1:99 weight % to about 99:1 weight %, based on the total weight of the copolymer. According to the instant invention, the weight ratio of monomer Ib to monomer II is from about 10:90 weight % to about 90:10 weight %, based on the total weight of the polymer. According to the instant invention, weight ratio of monomer Ib to monomer II is from about 25:75 weight % to about 75:25 weight %, based on the total weight of the polymer. According to the instant invention, weight ratio of monomer Ib to monomer II is from about 50:50 weight %, based on the total weight of the polymer.

The preparation of the cationic polymers of component (a) (i) for the inventive dye-polymer complex can be carried out using various polymerization techniques such as solution, emulsion, microemulsion, inverse emulsion, and/or bulk polymerization, as well as other technologies that are available to those who are skilled in the art. The polymerizations can be carried out with or without free radical initiators and with various initiator concentrations. The co- or terpolymers can also be prepared in such a way that the architecture of the polymers is random, block, alternating or core-shell, and with or without the use of polymerization regulators such as nitroxyl ethers or other types of nitroxyl radicals.

According to the instant invention, the weight average molecular weight of the cationic polymers of component (a) (i) is from about 1,000 to about 10 million Daltons. Another embodiment of the instant invention is cationic polymers of component (a) (i) having a weight average molecular weight from about 50,000 to about 5 million Daltons. Another embodiment of the instant invention is cationic polymers of component (a) (i) having a weight average molecular weight from about 200,000 to about 4 million Daltons. Another embodiment of the instant invention is cationic polymers of component (a) (i) having a weight average molecular weight from about 300,000 to about 2 million Daltons.

According to the instant invention, the anionic dyes of component (a) (ii) are not only those anionic dyes having at least one carboxylic acid function but also those having one or more sulfonic acid functions or anionic dyes having both one or more carboxylic acid functions and one or more sulfonic acid functions.

According to the instant invention, the anionic dyes of component (a) (ii) are selected from the group consisting of halogen-containing acid dyes, reactive dyes, azo dyes, anthraquinone dyes and other acid dyes.

An example of an anionic reactive dye according to the instant invention is Procion Red MX 5B.

According to the instant invention, the anionic dyes of component (a) (ii) are selected from the group consisting of D and C Red 21, D and C Orange 5, D and C Red 27, D and C Orange 10, D and C Red 3, D and C Red 7, D and C Red 6, D and C Red 2, D and C Red 4, D and C Red 8, D and C Red 33, D and C Yellow 5, D and C Yellow 6, D and C Green 5, D and C Yellow 10, D and C Green 3, D and C Blue 1, D and C Blue 2, D and C Violet 1, Food Black 1 (CI No. 28440), Acid Black 1 (CI No. 20470), Acid Black 2 (CI No. 50420), Food Red 10 (CI No. 18050), Food Blue 1 (CI No. 73015), Food Brown 3 (CI No. 20285), Food Red 3 (CI No. 14720), Food Red 7 (CI No. 16255), Food Yellow No. 4 (CI No. 19140), Food Yellow No. 13 (CI No. 47005), Red No. 102, Red No. 104-1, Red No. 105-1, Red No. 106, Yellow No. 5, Red No. 227, Red No. 230-1, Orange No. 205, Yellow No. 202-1, Yellow No. 203, Green No. 204, Blue No. 205, Brown No. 201, Red No. 401, Red No. 504, Orange No. 402, Yellow No. 403-1, Yellow No. 406, Yellow No. 407, Green No. 401, Violet No. 401, and Black No. 401, etc. In addition, natural acid dyes such as carminic acid and laccaic acid can be used.

Another embodiment of the instant invention is to employ a mixture of more than one anionic dye in component (a) (ii), such as those exemplified above.

Another embodiment of the instant invention is to employ a mixture of one or more anionic dyes of component (a) (ii) with other types of dyes in the dye-polymer complex.

Although there are no critical size limitations to the dye-polymer complex particles of component (a), the dye-polymer complex particles having a size of about 0.001 to about 500 micrometers are particularly advantageous. Another embodiment of the instant invention is a particle size for the dye-polymer complexes of about 0.01 to 300 micrometers. Another embodiment of the instant invention is a particle size for the dye-polymer complexes of about 1 to 300 micrometers.

According to the instant invention, the weight ratio of component (a) (i) to component (a) (ii) is from about 10,000:1 to about 1:10,000. According to the instant invention, the weight ratio of component (a) (i) to component (a) (ii) is from about 1,000:1 to about 1:1,000. According to the instant invention, the weight ratio of component (a) (i) to component (a) (ii) is from about 100:1 to about 1:100.

The term "effective colorizing amount" means for example the amount necessary to achieve the desired compositional color.

The dye-polymer complexes of component (a) of the personal care compositions preferably comprise no more than about 50 weight percent of the composition; more preferably no more than about 25 weight percent of the personal care composition; even more preferably no more than about 7 weight percent; and still more preferably no more than about 5 weight percent. The dye-polymer complexes of the personal care composition preferably comprise at least about 0.0001 weight percent of the personal care composition, more preferably at least about 0.01 weight percent, even more preferably at least about 0.1 weight percent, and still more preferably at least about 0.2 by weight of the composition.

The present personal care compositions may comprise further traditional additives, for example ultraviolet (UV) light absorbers and antioxidants.

Accordingly, the present invention further pertains to a personal care composition comprising
(a) an effective colorizing amount of one or more dye-polymer complexes formed from
(i) one or more cationic polymers and
(ii) one or more anionic dyes,
wherein components (a) (i) and (a) (ii) are complexed to form particles prior to addition to said personal care composition and wherein said complex remains as particles in the finished product;
(b) a cosmetically acceptable adjuvant; and
(c) at least one compound selected from the group consisting of ultraviolet light absorbers, antioxidants, tocopherol, tocopherol acetate, hindered amine light stabilizers, complex formers, optical brighteners, surfactants and polyorganosiloxanes.

The additional additives of present component (c) are for example those disclosed in co-pending U.S. application Ser. No. 09/830,788, filed May 1, 2001 and Ser. No. 09/830,787, filed May 1, 2001. The disclosures of these co-pending applications are hereby incorporated by reference. These applications are published as WO 00/25730 and WO 00/25731.

The UV (ultraviolet light) absorbers are for example selected from the group consisting of 2H-benzotriazoles, s-triazines, benzophenones, alpha-cyanoacrylates, oxanilides, benzoxazinones, benzoates and alpha-alkyl cinnamates.

The UV absorbers are, for example:
2,4,6-tris(2-hydroxy-4-octyloxyphenyl)-1,3,5-triazine;
2-(2,4-dihydroxyphenyl)-4,6-bis(2,4-dimethylphenyl)-1,3, 5-triazine;
2,4-bis(2-hydroxy-4-propyloxyphenyl)-6-(2,4-dimethylphenyl)-1,3,5-triazine;
2-(2-hydroxy-4-octyloxyphenyl)-4,6-bis(4-methylphenyl)-1,3,5-triazine;
2-(2-hydroxy-4-dodecyloxyphenyl)-4,6-bis(2,4-dimethylphenyl)-1,3,5-triazine;
2-[2-hydroxy-4-(2-hydroxy-3-butyloxypropyloxy)phenyl]-4,6-bis(2,4-dimethylphenyl)-1,3,5-triazine;
2-[2-hydroxy-4-(2-hydroxy-3-octyloxypropyloxy)phenyl]-4,6-bis(2,4-dimethylphenyl)-1,3,5-triazine;
2-[2-hydroxy-4-(2-hydroxy-3-tridecyloxy-propyloxy)phenyl]-4,6-bis(2,4-dimethylphenyl)-1,3,5-triazine;
5-chloro-2-(2-hydroxy-3,5-di-tert-butylphenyl)-2H-benzotriazole;
2-(2-hydroxy-3-dodecyl-5-methylphenyl)-2H-benzotriazole;
5-chloro-2-(2-hydroxy-3-tert-butyl-5-methylphenyl)-2H-benzotriazole;
bis-(3-(2H-benzotriazol-2-yl)-2-hydroxy-5-tert-octyl)methane;
2-(2-hydroxy-3,5-di-tert-butylphenyl)-2H-benzotriazole;
2-(2-hydroxy-3,5-di-tert-amylphenyl)-2H-benzotriazole;
2-(2-hydroxy-3,5-di-alpha-cumylphenyl)-2H-benzotriazole;
2-(2-hydroxy-3-alpha-cumyl-5-tert-octylphenyl)-2H-benzotriazole;
2-(2-hydroxy-5-tert-octylphenyl)-2H-benzotriazole;
3-(2H-benzotriazol-2-yl)-4-hydroxy-5-(1-methylpropyl)-benzenesulfonic acid monosodium salt;
3-tert-butyl-4-hydroxy-5-(2H-benzotriazol-2-yl)-hydrocinnamic acid and sodium salt;
12-hydroxy-3,6,9-trioxadodecyl 3-tert-butyl-4-hydroxy-5-(2H-benzotriazol-2-yl)-hydrocinnamate;
octyl 3-tert-butyl-4-hydroxy-5-(2H-benzotriazol-2-yl)-hydrocinnamate;
4,6-bis(2,4-dimethylphenyl)-2-(4-(3-dodecyloxy*-2-hydroxypropoxy)-2-hydroxyphenyl)-s-triazine (* is mixture of $C_{12-14}$oxy isomers);
4,6-bis(2,4-dimethylphenyl)-2-(4-octyloxy-2-hydroxyphenyl)-s-triazine;
2,4-dihydroxybenzophenone;
2,2'-dihydroxy-4,4'-dimethoxy-5,5'-disulfobenzophenone, disodium salt;
2-hydroxy-4-octyloxybenzophenone;
2-hydroxy-4-dodecyloxybenzophenone;
2,4-dihydroxybenzophenone;
2,2',4,4'-tetrahydroxybenzophenone;
4-aminobenzoic acid;
2,3-dihydroxypropyl-4-aminobenzoic acid;
3-(4-imidazolyl)acrylic acid;
2-phenyl-5-benzimidazole sulfonic acid;
N,N,N-trimethyl-alpha-(2-oxo-3-bornylidene)-p-toluidinium methyl sulfate;
5-benzoyl-4-hydroxy-2-methoxybenzenesulfonic acid, sodium salt;
3-(4-benzoyl-3-hydroxyphenoxy)-2-hydroxy-N,N,N-trimethyl-1-propanaminium chloride;
3-[4-(2H-benzotriazol-2-yl)-3-hydroxyphenoxy]-2-hydroxy-N,N,N-trimethyl-1-propanaminium, chloride;
2-(2-hydroxy-5-methylphenyl)-2H-benzotriazole; and
2,2'-dihydroxy-4,4'-dimethoxybenzophenone (Uvinul® 3049).

For instance, suitable UV absorbers are selected from:
3-(2H-benzotriazol-2-yl)-4-hydroxy-5-(1-methylpropyl)-benzenesulfonic acid monosodium salt;
3-tert-butyl-4-hydroxy-5-(2H-benzotriazol-2-yl)-hydrocinnamic acid and sodium salt;
2-(2-hydroxy-3,5-di-tert-butylphenyl)-2H-benzotriazole;
2-(2-hydroxy-3,5-di-tert-amylphenyl)-2H-benzotriazole;
4,6-bis(2,4-dimethylphenyl)-2-(4-(3-dodecyloxy*-2-hydroxypropoxy)-2-hydroxyphenyl)-s-triazine (* is mixture of $C_{12-14}$oxy isomers);
12-hydroxy-3,6,9-trioxadodecyl 3-tert-butyl-4-hydroxy-5-(2H-benzotriazol-2-yl)-hydrocinnamate;
2,4-dihydroxybenzophenone;

2,2'-dihydroxy-4,4'-dimethoxy-5,5'-disulfobenzophenone, disodium salt;

2,2',4,4'-tetrahydroxybenzophenone;

3-(4-benzoyl-3-hydroxyphenoxy)-2-hydroxy-N,N,N-trimethyl-1-propanaminium chloride;

3-[4-(2H-benzotriazol-2-yl)-3-hydroxyphenoxy]-2-hydroxy-N,N,N-trimethyl-1-propanaminium, chloride;

5-benzoyl-4-hydroxy-2-methoxy-benzenesulfonic acid, sodium salt; and 2-(2-hydroxy-3-alpha-cumyl-5-tert-octylphenyl)-2H-benzotriazole.

Additional suitable antioxidants are for example selected from the hindered phenolic and benzofuranone stabilizers.

Suitable antioxidants are, for example, selected from the group consisting of

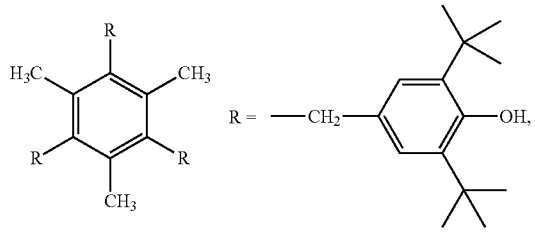

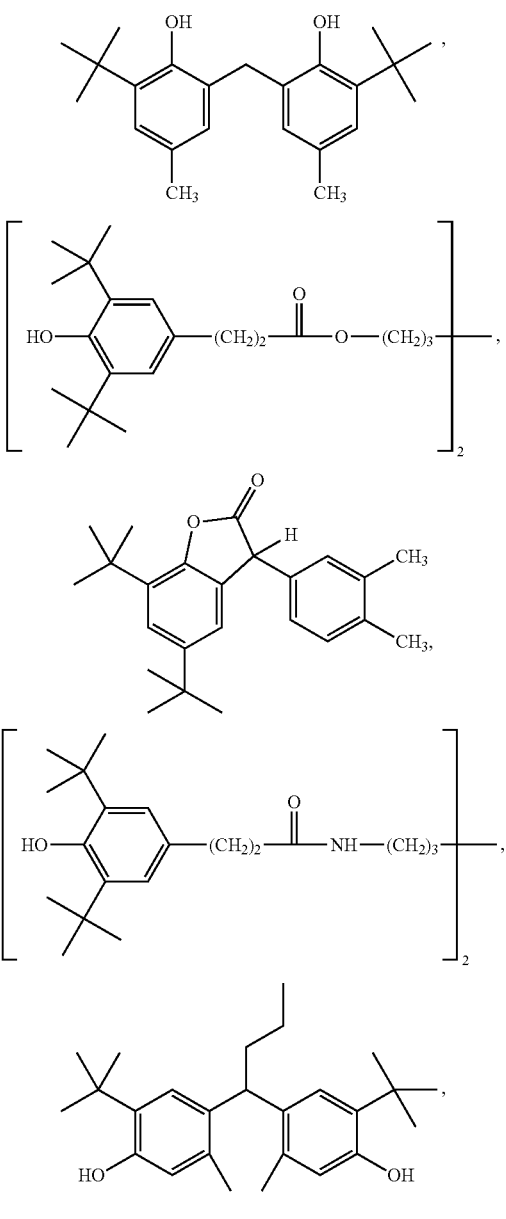

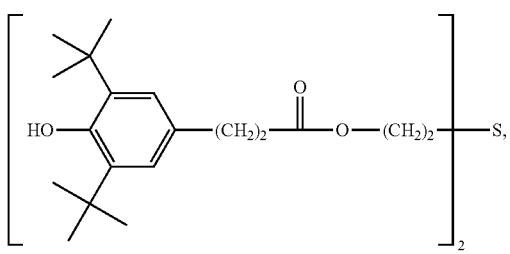
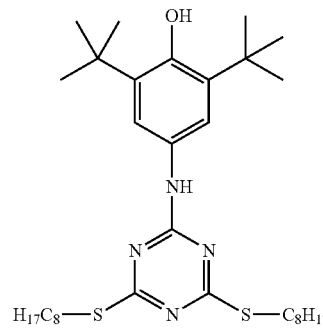
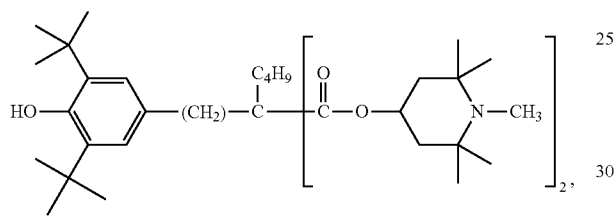
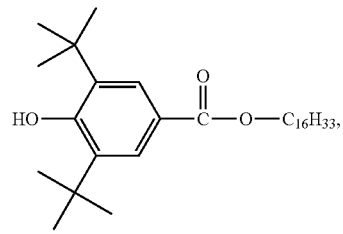
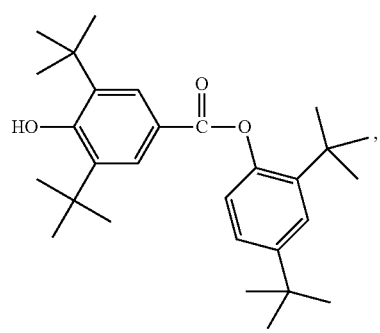
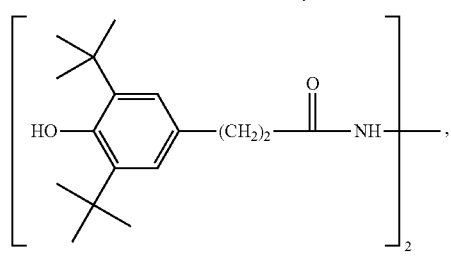
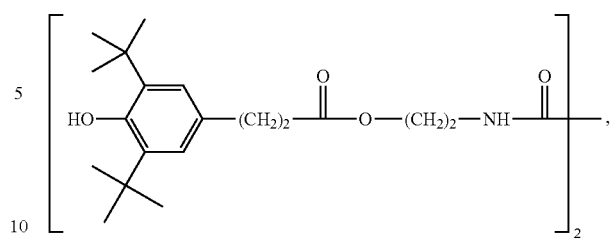
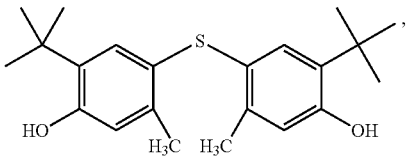
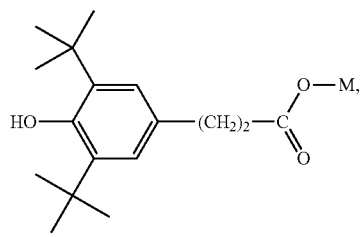
M = H, ammonium, alkali
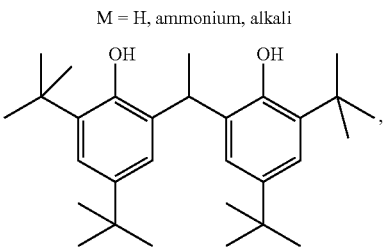
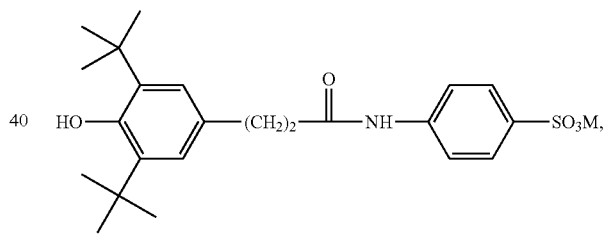
M = H, Na
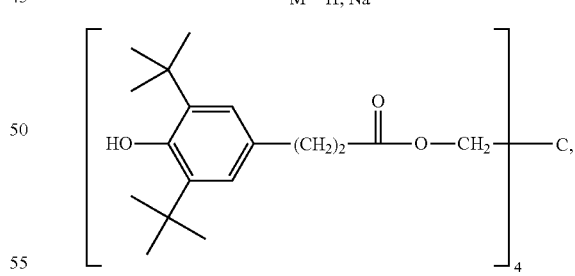
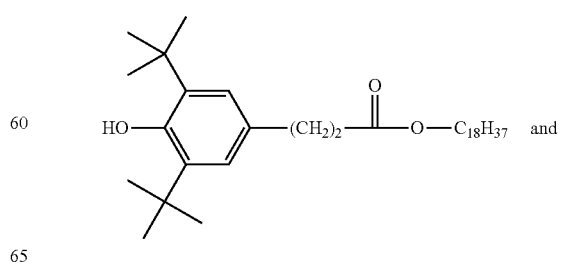
and

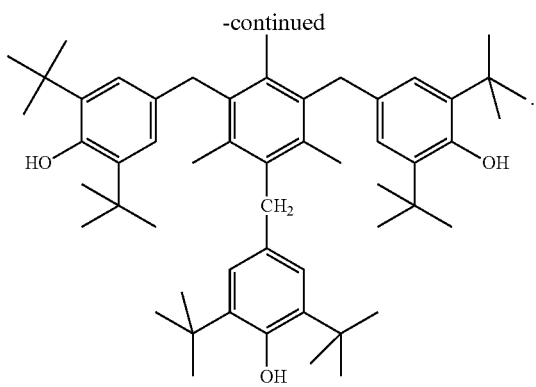

The hindered amine light stabilizers (HALS) of component (c) are for example known commercial compounds. They are for example selected from the group consisting of bis(2,2,6,6-tetramethylpiperidin-4-yl)sebacate, bis(2,2,6,6-tetramethylpiperidin-4-yl)succinate, bis(1,2,2,6,6-pentamethylpiperidin-4-yl)sebacate, n-butyl-3,5-di-tert-butyl-4-hydroxybenzylmalonic acid-bis(1,2,2,6,6-pentamethylpiperidyl)ester, the condensate of 1-hydroxyethyl-2,2,6,6-tetramethyl-4-hydroxypiperidine and succinic acid, the condensate of N,N'-bis(2,2,6,6-tetramethyl-4-piperidyl) hexamethylenediamine and 4-tert-octylamino-2,6-dichloro-1,3,5-s-triazine, tris(2,2,6,6-tetramethyl-4-piperidyl)nitrilotriacetate, tetrakis(2,2,6,6-tetramethyl-4-piperidyl)-1,2,3,4-butanetetraoate, 1,1'-(1,2-ethanediyl)-bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazaspiro[4.5]decane-2,4-dione, the condensate of N,N-bis(2,2,6,6-tetramethyl-4-piperidyl)hexamethylenediamine and 4-morpholino-2,6-dichloro-1,3,5-triazine, the condensate of 2-chloro-4,6-di(4-n-butylamino-2,2,6,6-tetramethylpiperidyl)-1,3,5-triazine and 1,2-bis(3-aminopropylamino) ethane, the condensate of 2-chloro-4,6-di(4-n-butylamino-1,2,2,6,6-pentamethylpiperidyl)-1,3,5-triazine and 1,2-bis(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidin-2,5-dione, 3-dodecyl-1-(1,2,2,6,6-pentamethyl-4-piperidyl)-pyrrolidine-2,5-dione, a mixture of 4-hexadecyloxy- and 4-stearyloxy-2,2,6,6-tetramethylpiperidine, the condensate of N,N'-bis(2,2,6,6-tetramethyl-4-piperidyl)hexamethylenediamine and 4-cyclohexylamino-2,6-dichloro-1,3,5-triazine, the condensate of 1,2-bis(3-aminopropylamino)ethane and 2,4,6-trichloro-1,3,5-triazine and 4-butylamino-2,2,6,6-tetramethylpiperidine (CAS reg. No. [136504-96-6]); (2,2,6,6-tetramethyl-4-piperidyl)-n-dodecylsuccinimide, (1,2,2,6,6-pentamethyl-4-piperidyl)-n-dodecylsuccinimide, 2-undecyl-7,7,9,9-tetramethyl-1-oxa-3,8-diaza-4-oxo-spiro[4,5]decane, the reaction product of 7,7,9,9-tetramethyl-2-cycloundecyl-1-oxa-3,8-diaza-4-oxospiro[4,5]decane and epichlorohydrin, tetra(2,2,6,6-tetramethylpiperidin-4-yl)-butane-1,2,3,4-tetracarboxylate, tetra(1,2,2,6,6-pentamethylpiperidin-4-yl)-butane-1,2,3,4-tetracarboxylate, 2,2,4,4-tetramethyl-7-oxa-3,20-diaza-21-oxo-dispiro[5.1.11.2]-heneicosan, 8-acetyl-3-dodecyl-1,3,8-triaza-7,7,9,9-tetramethylspiro[4,5]-decane-2,4-dione,

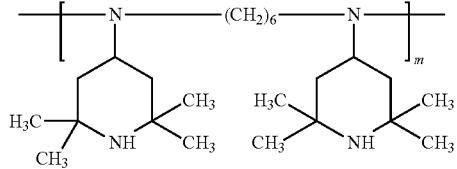

wherein m is a value from 5-50,

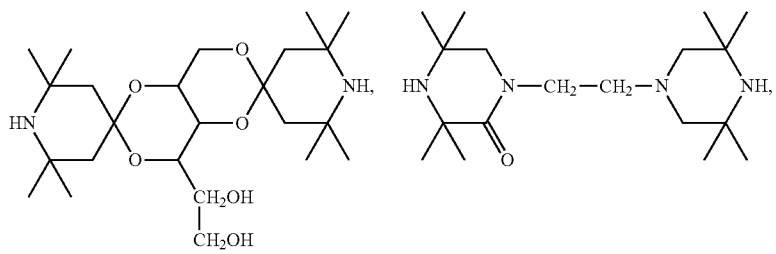

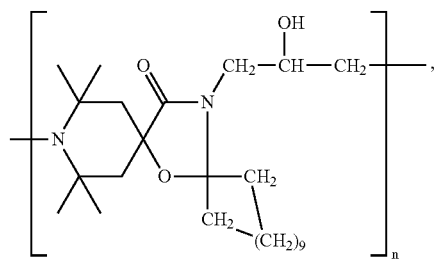

-continued

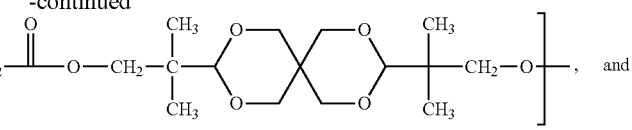
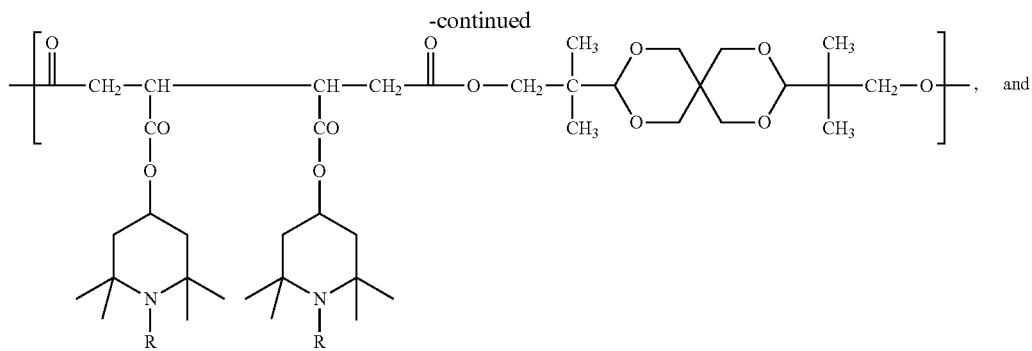

where R = H or CH₃

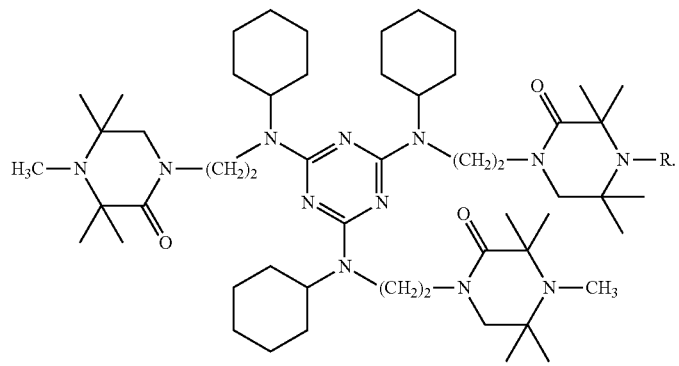

where R = H or CH₃

The complex formers of component (c) are for example nitrogen-containing complex formers or polyanionically-derived natural polysaccharides, for example those containing phosphate, phosphonate or methylphosphonate groups, such as chitin derivatives, e.g. sulfochitin, carboxymethylchitin, phosphochitin or chitosan derivatives, for example sulfochitosan, carboxymethylchitosan or phosphochitosan.

The complex formers of component (c) are, for example, selected from the group consisting of ethylenediaminetetracetic acid (EDTA), nitrilotriacetic acid (NTA), beta-alaninediacetic acid (EDETA) or ethylenediaminedisuccinic acid (EDDS),

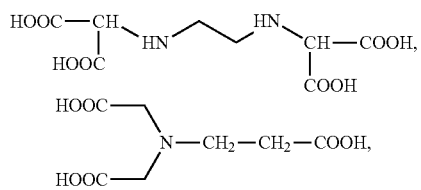

aminetrimethylenephosphoric acid (ATMP) conforming to formula

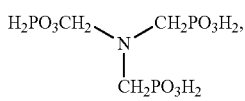

serinediacetic acid (SDA) conforming to formula

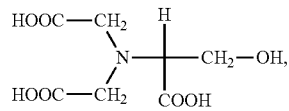

asparaginediacetic acid conforming to formula

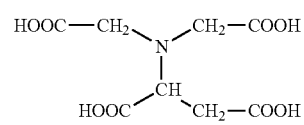

and methylglycinediacetic acid (MGDA) conforming to formula

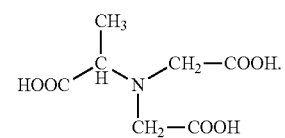

Component (c) of the personal care compositions preferably comprise no more than about 10 weight percent of the composition; more preferably no more than about 7 weight percent of the personal care composition; even more preferably no more than about 5 weight percent; and still more preferably no more than about 3 weight percent. The dye-polymer complexes of the personal care composition preferably comprise at least about 0.0001 weight percent of the personal care composition, more preferably at least about 0.01 weight percent, even more preferably at least about 0.1 weight percent, and still more preferably at least about 0.2 by weight of the composition.

The present dye-polymer complexes of component (a) are particularly suitable for colorizing personal care compositions or products, in particular for use in skin-care products, as bath and shower products, preparations containing fragrances and odoriferous substances, hair-care products, dentifrices, deodorizing and antiperspirant preparations, decorative preparations, light protection formulations and preparations containing active ingredients.

Suitable skin-care products are, in particular, body oils, body lotions, body gels, treatment creams, skin protection ointments, shaving preparations, such as shaving foams or gels, skin powders, such as baby powder, moisturising gels, moisturising sprays, revitalising body sprays, cellulite gels and peeling preparations.

Preparations containing fragrances and odoriferous substances are in particular scents, perfumes, and shaving lotions (aftershave preparations).

Suitable hair-care products are, for example, shampoos for humans and animals, in particular dogs and cats, hair conditioners, products for styling and treating hair, perming agents, hair sprays and lacquers, hair gels, hair fixatives and hair dyeing or bleaching agents.

Suitable dentifrices are in particular tooth creams, toothpastes, mouthwashes, mouth rinses, anti-plaque preparations and cleaning agents for dentures.

Suitable decorative preparations are in particular lipsticks, nail varnishes, eye shadows, mascaras, dry and moist make-up, rouge, powders, depilatory agents and suntan lotions.

Suitable cosmetic formulations containing active ingredients are in particular hormone preparations, vitamin preparations, vegetable extract preparations and antibacterial preparations.

The present personal care compositions or products can be in the form of creams, ointments, pastes, foams, gels, lotions, powders, make-ups, sprays, sticks or aerosols. The present dye-polymer complexes of component (a) may be present in the oil phase or in the aqueous or aqueous/alcoholic phase.

Creams are oil-in-water emulsions containing more than 50% water. The oil-containing base used therein is usually mainly fatty alcohols, for example lauryl, cetyl or stearyl alcohol, fatty acids, for example palmitic or stearic acid, liquid to solid waxes, for example isopropylmyristate or beeswax and/or hydrocarbon compounds, such as paraffin oil. Suitable emulsifiers are surfactants having primarily hydrophilic properties, such as the corresponding nonionic emulsifiers, for example fatty acid esters of polyalcohols of ethylene oxide adducts, such as polyglycerol fatty acid ester or polyoxyethylenesorbitan fatty acid ether (Tween trademarks); polyoxyethylene fatty alcohol ether or their esters or the corresponding ionic emulsifiers, such as the alkali metal salts of fatty alcohol sulfonates, sodium cetyl sulfate or sodium stearyl sulfate, which are usually used together with fatty alcohols, such as cetyl alcohol or stearyl alcohol. In addition, creams contain agents which reduce water loss during evaporation, for example polyalcohols, such as glycerol, sorbitol, propylene glycol, and/or polyethylene glycols.

Ointments are water-in-oil emulsions which contain up to 70%, for instance not more than 20 to 50%, of water or of an aqueous phase. The oil-containing phase contains predominantly hydrocarbons, such as paraffin oil and/or solid paraffin which for instance contains hydroxy compounds, for example fatty alcohol or their esters, such as cetyl alcohol or wool wax for improving the water absorption. Emulsifiers are correspondingly lipophilic substances, such as sorbitan fatty acid ester. In addition, the ointments contain moisturisers such as polyalcohols, for example glycerol, propylene glycol, sorbitol and/or polyethylene glycol as well as preservatives.

Rich creams are anhydrous formulations and are produced on the basis of hydrocarbon compounds, such as paraffin, natural or partially synthetic fats, for example coconut fatty acid triglycerides or, for instance, hardened oils and glycerol partial fatty acid esters.

Pastes are creams and ointments containing powdered ingredients which absorb secretions, for example metal oxides, such as titanium dioxide or zinc oxide, and also tallow and/or aluminium silicates which bind the moisture or the absorbed secretion.

Foams are liquid oil-in-water emulsions in aerosol form. Hydrocarbon compounds are used, inter alia, for the oil-containing phase, for example paraffin oil, fatty alcohols, such as cetyl alcohol, fatty acid esters, such as isopropylmyristate and/or waxes. Suitable emulsifiers are, inter alia, mixtures of emulsifiers having predominantly hydrophilic properties, for example polyoxyethylenesorbitan fatty acid ester, and also emulsifiers having predominantly lipophilic properties, for example sorbitan fatty acid ester. Commercially available additives are usually additionally employed, for example preservatives.

Gels are, in particular, aqueous solutions or suspensions of active substances in which gel formers are dispersed or swelled, in particular cellulose ethers, such as methyl cellulose, hydroxyethyl cellulose, carboxymethyl cellulose or vegetable hydrocolloids, for example sodium alginate, tragacanth or gum Arabic and polyacrylate thickener systems. The gels for example additionally contain polyalcohols, such as propylene glycol or glycerol as moisturisers and wetting agents, such as polyoxyethylenesobitan fatty acid ester. The gels furthermore contain commercially available preservatives, such as benzyl alcohol, phenethyl alcohol, phenoxyethanol and the like.

The following is a partial list of examples of personal care products of this invention and their ingredients:

| Body care product | Ingredients |
| --- | --- |
| moisturising cream | vegetable oil, emulsifier, thickener, perfume, water, antioxidant, UV absorbers |
| shampoo | surfactant, emulsifier, preservatives, perfume, antioxidant, UV absorbers |
| toothpaste | cleaning agent, thickener, sweetener, flavor, colorant, antioxidant, water, UV absorbers |
| lip-care stick | vegetable oil, wax, $TiO_2$, antioxidant, UV absorbers |

The present dye-polymer complexes of component (a) have high stability towards color changes and chemical degradation of the ingredients present in these products. For example, present compositions that further comprise additional dyes and/or pigments or mixtures thereof are found to have excellent color stability.

Accordingly, the present invention further pertains to a personal care composition comprising
 (a) an effective colorizing amount of one or more dye-polymer complexes formed from
  (i) one or more cationic polymers and
  (ii) one or more anionic dyes,
wherein components (a) (i) and (a) (ii) are complexed to form particles prior to addition to said personal care composition and wherein said complex remains as particles in the finished product; and (b) a cosmetically acceptable adjuvant, and
(d) a dye or a pigment or mixtures thereof.

Dyes of component (d) according to the present invention are for example:

disperse dyes which may be solubilzed in solvents like direct hair dyes of the HC type, for example HC Red No. 3, HC Blue No. 2 and all other hair dyes listed in International Cosmetic Ingredient Dictionary and Handbook, $7^{th}$ edition 19997) or the dispersion dyes listed in Color Index International or Society of Dyers and Colourists;

color varnishes (insoluble salts of soluble dyes, like many Ca—, Ba— or Al-salts of anionic dyes);

soluble anionic or cationic dyes, like acid dyes (anionic), basic dyes (cationic), direct dyes, reactive dyes or solvent dyes.

Generally, for the coloration of personal care compositions, all substances are suitable which have an absorption in the visible light of electromagnetic radiation (wavelength of ca. 4000 to 700 nm). The absorption is often caused by the following chromophores: Azo- (mono-, di, tris-, or poly-) stilbene-, carotenoide-, diarylmethan-, triarylmethan-, xanthen-, acridin-, quinoline, methin- (also polymethin-), thiazol-, indamin-, indophenol-, azin-, oxazin-, thiazin-, anthraquinone-, indigoid-, phtalocyanine- and further synthetic, natural and/or inorganic chromophores.

According to the instant invention, pigments of component d) include inorganic pigments, metal oxides and hydroxides, mica, organic pigments, pearlescent pigments, mineral silicates, porous materials, carbons, interference pigments, and the like.

Examples of the inorganic pigments of component (d) capable of being utilized according to the present invention are ultramarine blue, ultramarine violet, Prussian blue, manganese violet, titanium-coated mica, bismuth oxychloride, iron oxides, iron hydroxide, titanium dioxide, titanium lower oxides, chromium hydroxide and oxides, and carbon based pigments (e.g. Carbon Black). Of these inorganic pigments, ultramarine blue and Prussian blue are particular advantageous.

According to the instant invention, the range of useful organic pigments of component (d) may comprise monoazo, disazo, naphthol, dioxazone, azomethin, azocondensation, metal complex, nitro, perinone, quinoline, anthraquinone, benzimidozolone, isoindoline, isoindolinone, triarylmethane, quinacridone, hydroxyanthraquinone, aminoanthraquinone, anthrapyrimidine, indanthrone, flavanthrone, pyranthrone, anthanthrone, isoviolanthrone, diketopyrrolopyrrole, carbazole, indigo or thiolndigo pigments.

According to the instant invention, examples of the organic pigments of component (d) are C.I. 15850, C.I. 15850:1, C.I. 15585:1, C.I. 15630, C.I. 15880:1, C.I. 73360, C.I. 12085, C.I. 15865:2, C.I. 12075, C.I. 21110, C.I. 21095, and C.I. 11680, C.I. 74160 and zirconium, barium, or aluminum lakes of C.I. 45430, C.I. 45410, C.I. 45100, C.I. 17200, C.I. 45380, C.I. 45190, C.I. 14700, C.I. 15510, C.I. 19140, C.I. 15985, C.I. 45350, C.I. 47005, C.I. 42053, C.I. 42090.

C.I. means Colour Index as compiled by the by The Society of Dyers and Colourists and The American Association of Textile Chemists and Colourists.

According to the instant invention, mixtures of the organic pigments of component (d) may be used.

According to the instant invention, mixtures of the inorganic and organic pigments of component (d) may be used.

Component (d) of the personal care compositions preferably comprise no more than about 10 weight percent of the composition; more preferably no more than about 7 weight percent of the personal care composition; even more preferably no more than about 5 weight percent; and still more preferably no more than about 3 weight percent. The dye-polymer complexes of the personal care composition preferably comprise at least about 0.0001 weight percent of the personal care composition, more preferably at least about 0.01 weight percent, even more preferably at least about 0.1 weight percent, and still more preferably at least about 0.2 by weight of the composition.

Personal care compositions according to the invention may be generally applied to the skin and/or hair of humans and/or animals.

The present invention also pertains to a dye-polymer complex particle comprising
(i) one or more cationic polymers and
(ii) one or more anionic dyes,
wherein components (a) (i) and (a) (ii) are complexed to form particles prior to addition to a personal care composition or product and wherein said complex remains as particles in the finished product,
with the proviso that the cationic polymer of component (a) (i) is not a polyvinylamine hydrochloride homopolymer or is not a homopolymer of polydiallyidimethylammonium chloride with a molecular weight of less than 50,000 Daltons.

The present invention also pertains to a method of colorizing a personal care composition which comprises incorporating therein or applying thereto
(a) an effective colorizing amount of one or more dye-polymer complexes formed from
(i) one or more cationic polymers and
(ii) one or more anionic dyes,
wherein components (a) (i) and (a) (ii) are complexed to form particles prior to incorporating therein or applying thereto said personal care composition and wherein said complex remains as particles in the finished product,
with the proviso that the cationic polymer of component (a) (i) is not a polyvinylamine hydrochloride homopolymer or is not a homopolymer of polydiallyldimethylammonium chloride with a molecular weight of less than 50,000 Daltons.

The present invention also pertains to a method of colorizing a personal care product which additionally contains a dye and/or pigment or mixtures thereof, which comprises incorporating therein or applying thereto
(a) an effective colorizing amount of one or more dye-polymer complexes formed from
(i) one or more cationic polymers and
(ii) one or more anionic dyes,
wherein components (a) (i) and (a) (ii) are complexed to form particles prior to incorporating therein or applying thereto said personal care composition and wherein said complex remains as particles in the finished product,
with the proviso that the cationic polymer of component (a) (i) is not a polyvinylamine hydrochloride homopolymer or is not a homopolymer of polydiallyldimethylammonium chloride with a molecular weight of less than 50,000 Daltons.

The present colorizing methods do not include where the dye-polymer complex is formed during the colorizing process. For example, a printing process which comprises printing a non-complexed dye onto a paper with a dye fixative is excluded.

Personal care compositions according to the invention may be contained in a wide variety of personal care preparations.

Especially the following preparations, for example, come into consideration:

shaving preparations, e.g. shaving soap, foaming shaving creams, non-foaming shaving creams, foams and gels, preshave preparations for dry shaving, aftershaves or aftershave lotions;

skin-care preparations, e.g. skin emulsions, multi-emulsions or skin oils, body powders, hot-oil treatments, and exfoliating masques;

cosmetic personal care preparations, e.g. facial make-up in the form of lipsticks, eye shadow, eye liners, liquid make-up, day creams or powders, facial lotions, foundations, creams and powders (loose or pressed), hair removal systems;

light-protective preparations, such as sun tan lotions, creams and oils, sun blocks, pretanning preparations and sunless tanning preparations;

manicure preparations, e.g. nail polishes, nail enamels, enamel removers, nail treatments deodorants, e.g. deodorant sprays, pump-action sprays, deodorant gels, sticks or roll-ons;

antiperspirants, such as antiperspirant sticks, creams or roll-ons; and solid/liquid personal cleaning products, such as soap, cleansers, shampoo, conditioners, hair treatments.

Another embodiment of the instant invention is a personal care composition comprising said dye-polymer complexes which is formulated as a water-in-oil or oil-in-water emulsion, as an alcoholic or alcohol-containing formulation, as a vesicular dispersion of an ionic or non-ionic amphiphilic lipid, as a gel, or a solid stick as an aqueous or non-aqueous system.

Another embodiment of the instant invention is a personal care composition wherein the personal care or cosmetic composition additionally comprises a blend of pigment particles that are individually provided in a single matrix material.

The personal care compositions of the present invention may contain one or more additional skin care or hair care components. In a preferred embodiment, where the composition is to be in contact with human or animal keratinous tissue, the additional components should be suitable for application to keratinous tissue, that is, when incorporated into the composition they are suitable for use in contact with human or animal keratinous tissue without undue toxicity, incompatibility, instability, allergic response, and the like within the scope of sound medical judgment.

The instant compositions may further comprise, cosmetically acceptable ingredients and adjuvants of component (b) selected, in particular but not limited to, from among fatty substances, organic solvents, oil structurants, surfactants, emulsifiers, thickeners, organic cationic deposition polymers, demulcents, opacifiers, additional colorants colorants, effect pigments, additional stabilizers, emollients, antifoaming agents, moisturizing agents, antioxidants, vitamins, peptides, amino acids, botanical extracts, particulates, perfumes, preservatives, polymers, fillers, sequestrants, propellants, alkalinizing or acidifying agents or other optional ingredients customarily formulated into cosmetics or other personal care compositions according to the invention.

The fatty substances may be an oil or a wax or mixtures thereof, and they also comprise fatty acids, fatty alcohols and esters of fatty acids. The oils may be selected from among animal, vegetable, mineral or synthetic oils and, in particular, from among liquid paraffin, paraffin oil, silicone oils, volatile or otherwise, isoparaffins, polyolefins, fluorinated or perfluorinated oils. Likewise, the waxes may be animal, fossil, vegetable, mineral or synthetic waxes which are also known per se.

Exemplary organic solvents may include the lower alcohols and polyols.

Of course, one skilled in this art will take care to select this or these optional additional compounds and/or their quantities such that the advantageous properties, in particular the resistance to water, the stability, which are intrinsically associated with the sunscreen compositions in accordance with the invention are not, or not substantially, altered by the addition(s) envisaged.

The CTFA Cosmetic Ingredient Handbook, Second Edition (1992) describes a wide variety of non-limiting cosmetic and pharmaceutical ingredients commonly used in the personal care industry, which are suitable for use in the personal care compositions of the present invention.

The present invention may optionally comprise an oil structurant. The structurant can provide the dispersed phase with the correct rheological properties. This can aid in providing effective deposition and retention to the skin, the structured oil or oil phase should have a viscosity in the range of 100 to about 200,000 poise measured at 1 Sec-1, preferably 200 to about 100,000 poise, and most preferably 200 to about 50,000 poise. The amount of structurant required to produce this viscosity will vary depending on the oil and the structurant, but in general, the structurant will preferably be less than 75 weight percent of the dispersed oil phase, more preferably less than 50 weight percent, and still more preferably less than 35 weight percent of the dispersed oil phase.

The structurant can be either an organic or inorganic structurant. Examples of organic thickeners suitable for the invention are solid fatty acid esters, natural or modified fats, fatty acid, fatty amine, fatty alcohol, natural and synthetic waxes, and petrolatum, and the block copolymers sold under the name KRATON by Shell. Inorganic structuring agents include hydrophobically modified silica or hydrophobically modified clay. Nonlimiting examples of inorganic structurants are BENTONE 27V, BENTONE 38V or BENTONE GEL MIO V from Rheox; and CAB-O-SIL TS720 or CAB-O-SIL M5 from Cabot Corporation.

Structurants meeting the above requirements with the selected skin compatible oil can form 3-dimensional network to build up the viscosity of the selected oils. It has been found that such structured oil phases, i.e., built with the 3-dimensional network, are extremely desirable for use as wet-skin treatment compositions used in bathing. These structured oils can deposit and be retained very effectively on wet skin and retained after rinsing and drying to provide long-lasting after wash skin benefit without causing a too oily/greasy wet and dry feel. It is believed that the highly desirable in-use and after-use properties of such structured oils are due to their shear thinning rheological properties and the weak structure of the network. Due to its high low-shear viscosity, the 3-dimensional network structured oil can stick and retain well on the skin during application of the skin conditioner. After being deposited on the skin, the network yields easily during rubbing due to the weak structuring of the crystal network and its lower high-shear viscosity.

A wide variety of surfactants can be useful herein, both for emulsification of the dispersed phase as well as to provide acceptable spreading and in use properties for non-lathering systems. For cleansing applications, the surfactant phase also serves to clean the skin and provide an acceptable amount of lather for the user. The composition preferably contains no more than about 50 weight percent of a surfactant, more preferably no more than about 30 weight percent, still more preferably no more than about 15 weight percent, and even more preferably no more than about 5 weight percent of a surfactant. The composition preferably contains at least about 5 weight percent of a surfactant, more preferably at least about 3 weight percent, still more preferably at least about 1 weight percent, and even more preferably at least about 0.1 weight percent of a surfactant. For cleansing applications the personal care compositions preferably produces a Total Lather Volume of at least 300 ml, more preferably greater than 600 ml as described in the Lathering Volume Test. The personal care compositions preferably produces a Flash Lather Volume of at least 100 ml, preferably greater than 200 ml, more preferably greater than 300 ml as described in the Lathering Volume Test.

Preferable surfactants useful in the personal care compositions of the instant invention include those selected from the group consisting of anionic surfactants, nonionic surfactants, amphoteric surfactants, non-lathering surfactants, emulsifiers and mixtures thereof. Non-limiting examples of surfactants useful in the compositions of the present invention are disclosed in U.S. Pat. No. 6,280,757, to McAtee et al., issued Aug. 28, 2001.

Non-limiting examples of anionic surfactants useful in the personal care compositions of the present invention are disclosed in McCutcheon's, Detergents and Emulsifiers, North American edition (1986), published by Allured Publishing Corporation; McCutcheon's, Functional Materials, North American Edition (1992); and U.S. Pat. No. 3,929,678, to Laughlin et al., issued Dec. 30, 1975.

A wide variety of anionic surfactants are useful herein. Non-limiting examples of anionic surfactants include those selected from the group consisting of sarcosinates, sulfates, isethionates, taurates, phosphates, lactylates, glutamates, and mixtures thereof. Amongst the isethionates, the alkoyl isethionates are preferred, and amongst the sulfates, the alkyl and alkyl ether sulfates are preferred.

Other anionic materials useful herein are fatty acid soaps (i.e., alkali metal salts, e.g., sodium or potassium salts) typically having from a fatty acid having about 8 to about 24 carbon atoms, preferably from about 10 to about 20 carbon atoms. These fatty acids used in making the soaps can be obtained from natural sources such as, for instance, plant or animal-derived glycerides (e.g., palm oil, coconut oil, soybean oil, castor oil, tallow, lard, etc.) The fatty acids can also be synthetically prepared. Soaps and their preparation are described in detail in U.S. Pat. No. 4,557,853.

Other anionic materials include phosphates such as monoalkyl, dialkyl, and trialkylphosphate salts. Non-limiting examples of preferred anionic lathering surfactants useful herein include those selected from the group consisting of sodium lauryl sulfate, ammonium lauryl sulfate, ammonium laureth sulfate, sodium taureth sulfate, sodium trideceth sulfate, ammonium cetyl sulfate, sodium cetyl sulfate, ammonium cocoyl isethionate, sodium lauroyl isethioriate, sodium lauroyl lactylate, triethanolamine lauroyl lactylate, sodium caproyl lactylate, sodium lauroyl sarcosinate, sodium myristoyl sarcosinate, sodium cocoyl sarcosinate, sodium lauroyl methyl taurate, sodium cocoyl methyl taurate, sodium lauroyl glutamate, sodium myristoyl glutamate, and sodium cocoyl glutamate and mixtures thereof.

Especially preferred for use herein are ammonium lauryl sulfate, ammonium laureth sulfate, sodium lauroyl sarcosinate, sodium cocoyl sarcosinate, sodium myristoyl sarcosinate, sodium lauroyl lactylate, and triethanolamine lauroyl lactylate.

Non-limiting examples of nonionic surfactants for use in the personal care compositions of the present invention are disclosed in McCutcheon's, Detergents and Emulsifiers, North American edition (1986), published by Allured Publishing Corporation; and McCutcheon's, Functional Materials, North American Edition (1992).

Nonionic surfactants useful herein include those selected from the group consisting of alkyl glucosides, alkyl polyglucosides, polyhydroxy fatty acid amides, alkoxylated fatty acid esters, sucrose esters, amine oxides, and mixtures thereof.

Non-limiting examples of preferred nonionic surfactants for use herein are those selected from the group consisting of C8-C14 glucose amides, C8-C14 alkyl polyglucosides, sucrose cocoate, sucrose laurate, lauramine oxide, cocoamine oxide and mixtures thereof.

The term "amphoteric surfactant," as used herein, is also intended to encompass zwitterionic surfactants, which are well known to formulators skilled in the art as a subset of amphoteric surfactants.

A wide variety of amphoteric lathering surfactants can be used in the personal care compositions of the present invention. Particularly useful are those which are broadly described as derivatives of aliphatic secondary and tertiary amines, preferably wherein the nitrogen is in a cationic state, in which the aliphatic radicals can be straight or branched chain and wherein one of the radicals contains an ionizable water solubilizing group, e.g., carboxy, sulfonate, sulfate, phosphate, or phosphonate.

Non-limiting examples of amphoteric surfactants useful in the compositions of the present invention are disclosed in McCutcheon's, Detergents and Emulsifiers, North American edition (1986), published by Allured Publishing Corporation; and McCutcheon's, Functional Materials, North American Edition (1992).

Non-limiting examples zwitterionic surfactants are those selected from the group consisting of betaines, sultaines, hydroxysultaines, alkyliminoacetates, iminodialkanoates, aminoalkanoates, and mixtures thereof.

Preferred surfactants for use herein are the following, wherein the anionic surfactant is selected from the group consisting of ammonium lauroyl sarcosinate, sodium trideceth sulfate, sodium lauroyl sarcosinate, ammonium laureth sulfate, sodium laureth sulfate, ammonium lauryl sulfate, sodium lauryl sulfate, ammonium cocoyl isethionate, sodium cocoyl isethionate, sodium lauroyl isetlionate, sodium cetyl sulfate, sodium lauroyl lactylate, triethanolamine lauroyl lactylate, and mixtures thereof, wherein the non-ionic surfactant is selected from the group consisting of lauramine oxide, cocoamine oxide, decyl polyglucose, lauryl polyglucose, sucrose cocoate, C12-14 glucosamides, sucrose laurate, and mixtures thereof; and wherein the amphoteric surfactant is selected from the group consisting of disodium lauroamphodiacetate, sodium lauroamphoacetate, cetyl dimethyl betaine, cocoamidopropyl betaine, cocoamidopropyl hydroxy sultaine, and mixtures thereof.

A wide variety of non-lathering surfactants are useful herein. The personal care compositions of the present invention can comprise a sufficient amount of one or more non-lathering surfactants to emulsify the dispersed phase to yield an appropriate particle size and good application properties on wet skin.

Nonlimiting examples of these non-lathering compositions are: polyethylene glycol 20 sorbitan monolaurate (Polysorbate 20), polyethylene glycol 5 soya sterol, Steareth-20, Ceteareth-20, PPG-2 methyl glucose ether distearate, Ceteth-10, Polysorbate 80, cetyl phosphate, potassium cetyl phosphate, diethanolamine cetyl phosphate, Polysorbate 60, glyceryl stearate, PEG-100 stearate, polyoxyethylene 20 sorbitan trioleate (Polysorbate 85), sorbitan monolaurate, polyoxyethylene 4 lauryl ether sodium stearate, polyglyceryl-4 isostearate, hexyl laurate, steareth-20, ceteareth-20, PPG-2 methyl glucose ether distearate, ceteth-10, diethanolamine cetyl phosphate, glyceryl stearate, PEG-100 stearate, and mixtures thereof.

In addition, there are several commercial emulsifier mixtures that are useful in some embodiments of the personal care compositions according to the present invention.

Examples include PROLIPID 141 (glyceryl stearate, behenyl alcohol, palmitic acid, stearic acid, lecithin, lauryl alcohol, myristyl alcohol and cetyl alcohol) and 151 (Glyceryl stearate, cetearyl alcohol, stearic acid, 1-propanamium, 3-amino-N-(2-(hydroxyethyl-)-N-N-Dimethyl,N-C(16-18) Acyl Derivatives, Chlorides) from ISP; POLAWAX NF (Emulsifying wax NF), INCROQUAT BEHENYL TMS (behentrimonium sulfate and cetearyl alcohol) from Croda; and EMULLIUM DELTA (cetyl alcohol, glyceryl stearate, PEG-75 stearate, ceteth-20 and steareth-20) from Gattefosse.

The personal care compositions of the present invention, in some embodiments, may further include one or more thickening/aqueous phase stability agents. Because different stability agents thicken with different efficiencies, it is difficult to provide an accurate compositional range, however, when present, the composition preferably comprises no more than about 20 weight percent, more preferably no more than about 10 weight percent, more preferably no more than about 8 weight percent, and still more preferably no more than about 7 weight percent of the personal care composition. When present, the thickening/aqueous phase stability agent preferably comprises at least about 0.01 weight percent, more preferably at least about 0.05 weight percent, and still more preferably at least about 0.1 weight percent of the personal care composition. A better method of describing the stability agent is to say that it must build viscosity in the product. This can be measured using the Stability Agent Viscosity Test; preferably, the stability agent produces a viscosity in this test of at least 1000 cps, more preferably at least 1500 cps, and still more preferably at least 2000 cps.

Nonlimiting examples of thickening agents useful herein include carboxylic acid polymers such as the carbomers (such as those commercially available under the trade name CARBOPOL® 900 series from B.F. Goodrich; e.g., CARBOPOL® 954). Other suitable carboxylic acid polymeric agents include copolymers of C10-30 alkyl acrylates with one or more monomers of acrylic acid, methacrylic acid, or one of their short chain (i.e., C1-4 alcohol) esters, wherein the cross linking agent is an allyl ether of sucrose or pentaerytritol. These copolymers are known as acrylates/C10-30 alkyl acrylate crosspolymers and are commercially available as CARBOPOL® 1342, CARBOPOL® (1382, PEMULEN TR-1, and PEMULEN TR-2, from B.F. Goodrich.

Other nonlimiting examples of thickening agents include crosslinked polyacrylate polymers including both cationic and nonionic polymers.

Still other nonlimiting examples of thickening agents include the polyacrylamide polymers, especially nonionic polyacrylamide polymers including substituted branched or unbranched polymers. More preferred among these polyacrylamide polymers is the nonionic polymer given the CTFA designation polyacrylamide and isoparaffin and laureth-7, available under the Trade name SEPIGEL 305 from Seppic Corporation (Fairfield, N.J.). Other polyacrylamide polymers useful herein include multi-block copolymers of acrylamides and substituted acrylamides with acrylic acids and substituted acrylic acids. Commercially available examples of these multi-block copolymers include HYPAN SR150H, SS500V, SS500W, SSSA100H, from Lipo Chemicals, Inc., (Patterson, N.J.).

Another nonlimiting class of thickening agents useful herein is the polysaccharides. Nonlimiting examples of polysaccharide gelling agents include those selected from cellulose, and cellulose derivatives. Preferred among the alkyl hydroxyalkyl cellulose ethers is the material given the CTFA designation cetyl hydroxyethylcellulose, which is the ether of cetyl alcohol and hydroxyethylcellulose, sold under the trade name NATROSEL® CS PLUS from Aqualon Corporation (Wilmington, Del.). Other useful polysaccharides include scleroglucans which are a linear chain of (1-3) linked glucose units with a (1-6) linked glucose every three units, a commercially available example of which is CLEAROGEL™ CS 11 from Michel Mercier Products Inc. (Mountainside, N.J.).

Another nonlimiting class of thickening agents useful herein is the gums. Nonlimiting examples of gums useful herein include hectorite, hydrated silica, xantham gum, cellulose gums, guar gum, biosaccharide gums and mixtures thereof.

Yet another nonlimiting class of thickening agents useful herein is the modified starches. Acrylate modified starches such as WATERLOCK® from Grain Processing Corporation may be used. Hydroxypropyl starch phosphate, tradename STRUCTURE XL from National Starch is another example of a useful modified starch, and other useful examples include ARISTOFLEX HMB (Ammonium Acrylodimethyltaruate/Beheneth-25 Methacrylate Crosspolymer) from Clariant and cationic stabylens.

The personal care compositions according to the present invention may also contain organic cationic deposition polymers. Concentrations of the cationic deposition polymers preferably range from about 0.025% to about 10%, more preferably from about 0.05% to about 2%, even more preferably from about 0.1% to about 1%, by weight of the personal care composition.

Suitable cationic deposition polymers for use in the present invention contain cationic nitrogen-containing moieties such as quaternary ammonium or cationic protonated amino moieties. The cationic protonated amines can be primary, secondary, or tertiary amines (preferably secondary or tertiary), depending upon the particular species and the selected pH of the personal care composition. The average molecular weight of the cationic deposition polymer is between about 5,000 to about 10 million, preferably at least about 100,000, more preferably at least about 200,000, but preferably not more than about 2 million, more preferably not more than about 1.5 million. The polymers also have a cationic charge density ranging from about 0.2 meq/gm to about 5 meq/gm, preferably at least about 0.4 meq/gm, more preferably at least about 0.6 meq/gm., at the pH of intended use of the personal care composition, which pH will generally range from about pH 4 to about pH 9, preferably between about pH 5 and about pH 8.

Nonlimiting examples of cationic deposition polymers for use in the personal care compositions include polysaccharide polymers, such as cationic cellulose derivatives. Preferred cationic cellulose polymers are the salts of hydroxyethyl cellulose reacted with trimethyl ammonium substituted epoxide, referred to in the industry (CTFA) as Polyquatemium 10 which are available from Amerchol Corp. (Edison, N.J., USA) in their Polymer KG, JR and LR series of polymers with the most preferred being KG-30M.

Other suitable cationic deposition polymers include cationic guar gum derivatives, such as guar hydroxypropyltrimonium chloride, specific examples of which include the Jaguar series (preferably Jaguar C-17) commercially available from Rhodia Inc., and N-Hance polymer series commercially available from Aqualon.

Other suitable cationic deposition polymers include synthetic cationic polymers. The cationic polymers suitable for use in the personal cleansing composition herein are water soluble or dispersible, non cross linked, cationic polymers having a cationic charge density of from about 4 meq/gm to about 7 meq/gm, preferably from about 4 meq/gm to about 6 meq/gm, more preferably from about 4.2 meq/gm to about 5.5 meq/gm. The select polymers also must have an average molecular weight of from about 1,000 to about 1 million, preferably from about 10,000 to about 500,000, more preferably from about 75,000 to about 250,000.

A non limiting example of a commercially available synthetic cationic polymer for use in the cleansing compositions is polymethyacrylamidopropyl trimonium chloride, available under the trade name POLYCARE 133, from Rhodia, Cranberry, N.J., U.S.A.

Other non limiting examples of optional ingredients include benefit agents that are selected from the group consisting of vitamins and derivatives thereof (e.g., ascorbic acid, vitamin E, tocopheryl acetate, and the like); sunscreens; thickening agents (e.g., polyol alkoxy ester, available as CROTHIX from Croda); preservatives for maintaining the anti microbial integrity of the cleansing compositions; anti-acne medicaments (resorcinol, salicylic acid, and the like); antioxidants; skin soothing and healing agents such as aloe vera extract, allantoin and the like; chelators and sequestrants; and agents suitable for aesthetic purposes such as fragrances, essential oils, skin sensates, pigments, pearlescent agents (e.g., mica and titanium dioxide), lakes, colorings, and the like (e.g., clove oil, menthol, camphor, eucalyptus oil, and eugenol), antibacterial agents and mixtures thereof. These materials can be used at ranges sufficient to provide the required benefit, as would be obvious to one skilled in the art.

The following examples describe certain embodiments of this invention, but the invention is not limited thereto. It should be understood that numerous changes to the disclosed embodiments could be made in accordance with the disclosure herein without departing from the spirit or scope of the invention. These examples are therefore not meant to limit the scope of the invention. Rather, the scope of the invention is to be determined only by the appended claims and their equivalents. In these examples all parts given are by weight unless otherwise indicated.

EXAMPLE 1

D&C Red 4 Dye Complex with polyepiamine

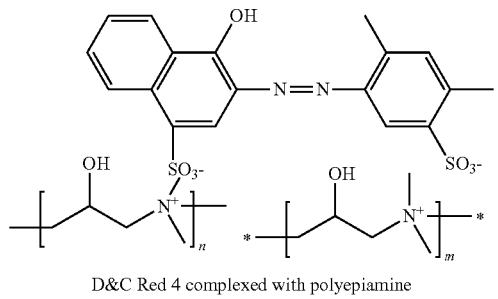

D&C Red 4 complexed with polyepiamine

Polyepiamine copolymer is an aqueous solution polymer containing 50% of branched polyepiamine prepared by step polymerization of epichlorohydrin and dimethylamine with small amount of ethylenediamine as a crosslinker. The polyepiamine copolymer possesses a viscosity of 4500 to 9000 cps measured at 25 C using a Brookfield viscometer, spindle LV3 and 12 rpm. Typical weight average molecular weight (MW) is estimated to be about 250,000 Daltons by GPC using polyethylene oxide MW standards.

To a 250 mL beaker with stirring are added D&C Red #4 Dye (2.1424 g, Puricolor, Ciba Specialty Chemicals) and deionized water (89.27 g) in order to prepare a 3 wt % dye solution (A). Solution B containing 3% by weight of the polyepiamine copolymer, described above, is prepared by diluting the polyepiamine copolymer solution with deionized water to the proper concentration. Solution A (71.74 g, 3% D&C Red 4 dye) is slowly added to solution B (71.72 g, 3% polyepiamine copolymer) with agitation. After five minutes of agitation, the mixture thickens and precipitation occurs. At this point, deionized water (20 g) is added and agitation is continued for another 10 minutes. The thick red slurry obtained is vacuum filtered though #1 filter paper. The filter cake is washed twice with copious amounts of deionized water until little or no color is observed in the filtrate. The filter cake is vacuum oven dried at 70 C overnight and then mortar grinded to yield about 3 g of dried red powder dye complex.

The final dye-polymer complex powder (0.1 g) is placed in 10 mL of deionized water. Red dye-polymer complex dispersion is agitated briefly. It takes about one week for the dye complex powder to completely settle. After two weeks of standing at room temperature, there is little to no color bleeding and the water phase remained colorless clear.

EXAMPLE 2

D&C Red 4 Dye Complex with Poly-DADMAC

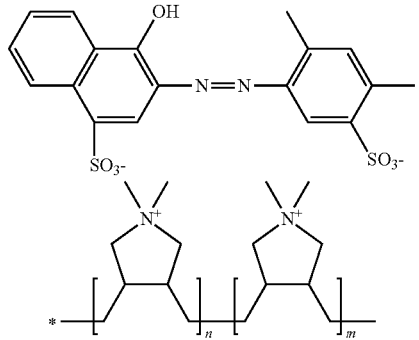

D&C Red 4 complexed with poly-DADMAC

Poly-DADMAC is an aqueous solution of 20% by weight of a linear homopolymer of DADMAC with a Brookfield viscosity of 1600 to 3000 cps. The weight average molecular weight is, determined by GPC with PEO standards, about 500,000 Daltons.

According to the dye complexation procedure of Instant Example 1, the instant dye-polymer complex is formed between D&C Red 4 and a linear homopolymer of DAD-MAC.

EXAMPLE 3

D&C Red 4 Dye Complex with Co-polyDADMAC-copolymethylmethacrylate

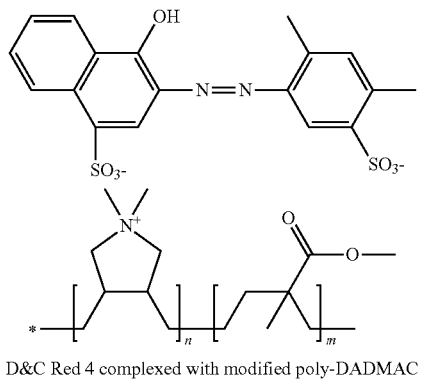

D&C Red 4 complexed with modified poly-DADMAC

A 1-liter reactor equipped with a condenser, a thermometer, a nitrogen inlet, and an overhead agitator is charged with DADMAC monomer (453.8 g, 66% assay), methyl methacrylate (MMA, 15.8 g), deionized water (57.4 g) and Na$_4$EDTA (0.15 g, 20% assay). The polymerization mixture is purged with nitrogen and heated with agitation to a temperature of 90 C. An aqueous solution containing ammonium persulfate (APS, 5.1 g) is slowly fed to the reactor over 190 minutes. The reaction temperature is allowed to increase to above 100 C and then maintained at reflux temperature (100-110 C) during the APS feed period. After the APS feed, the reaction temperature is lowered to and held at 95 C for about 30 minutes. At this point, an aqueous solution containing sodium metabisufite (MBS, 5.6 g) is added over 30 minutes. The reactor content temperature is held at 95 C for another 30 minutes to complete the polymerization (above 99% conversion). The polymer solution is diluted with sufficient deionized water to achieve a concentration of about 35% solids and cooled to room temperature. Total monomer conversion is measured to be above 99.5%. The final product has a Brookfield viscosity of 23,400 cps at 25° C. and 33.7% polymer solids.

According to the dye complexation procedure of Instant Example 1, the instant dye-polymer complex is formed between D&C Red 4 and the copolymer of DADMAC and methylmethacrylate.

EXAMPLE 4

D&C Red 4 Dye Complex with Co-polyDADMAC-copolymethylmethacrylate

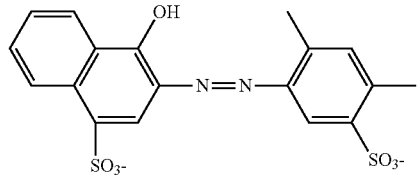

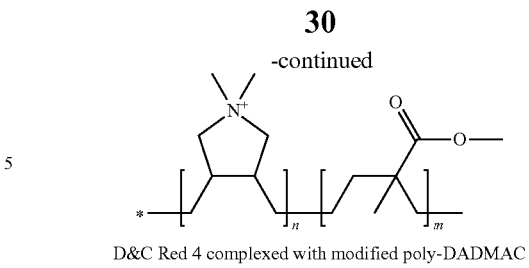

D&C Red 4 complexed with modified poly-DADMAC

A 1-liter reactor equipped with a condenser, a thermometer, a nitrogen inlet, and an overhead agitator is charged with DADMAC monomer (453.8 g, 66% assay), methyl methacrylate (MMA, 31.6 g), deionized water (57.4 g) and Na$_4$EDTA (0.15 g, 20% assay). The polymerization mixture is purged with nitrogen and heated with agitation to a temperature of 90 C. An aqueous solution containing ammonium persulfate (APS, 5.1 g) is slowly fed to the reactor over 190 minutes. The reaction temperature is allowed to increase to above 100 C and then maintained at reflux temperature (100-110 C) during the APS feed period. After the APS feed, the reaction temperature is lowered to and held at 95 C for about 30 minutes. At this point, an aqueous solution containing sodium metabisufite (MBS, 5.6 g) is added over 30 minutes. The reactor content temperature is held at 95 C for another 30 minutes to complete the polymerization (above 99% conversion). The polymer solution is diluted with sufficient deionized water to achieve a concentration of about 35% solids and cooled to room temperature. Total monomer conversion is measured to be above 99.5%. The final product has a Brookfield viscosity of 5300 cps at 25° C. and 35.1% polymer solids.

According to the dye complexation procedure of Instant Example 1, the instant dye-polymer complex is formed between D&C Red 4 and the copolymer of DADMAC and methyl methacrylate.

EXAMPLE 5

D&C Red 4 Dye Complex with Co-polyDADMAC-copolystyrene

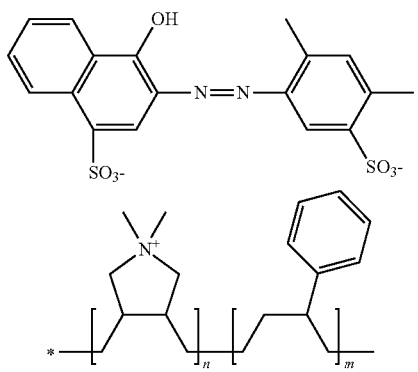

D&C Red 4 complexed with modified poly-DADMAC

A 1-liter reactor equipped with a condenser, a thermometer, a nitrogen inlet, and an overhead agitator is charged with DADMAC monomer (453.8 g, 66% assay), styrene (7.9 g), deionized water (57.4 g) and Na$_4$EDTA (0.15 g, 20% assay). The polymerization mixture is purged with nitrogen and heated with agitation to a temperature of 90 C. An aqueous solution containing ammonium persulfate (APS, 5.1 g) is slowly fed to the reactor over 190 minutes. The reaction temperature is allowed to increase to above 100 C and then maintained at reflux temperature (100-110 C) during the APS feed period. After the APS feed, the reaction temperature is lowered to and held at 95 C for about 30 minutes. At this point, an aqueous solution containing sodium metabisufite (MBS, 5.6 g) is added over 30 minutes. The reactor content temperature is held at 95 C for another 30 minutes to complete the polymerization (above 99% conversion). The polymer solution is diluted with sufficient deionized water to achieve a concentration of about 35% solids and cooled to room temperature. Total monomer conversion is measured to be above 99.5%. The final product has a Brookfield viscosity of 2830 cps at 25° C. and 36.5% polymer solids.

According to the dye complexation procedure of Instant Example 1, the instant dye-polymer complex is formed between D&C Red 4 and the copolymer of DADMAC and styrene.

EXAMPLE 6

D&C Red 4 Dye Complex with
Co-polyDADMAC-copolybenzylmethacrylate

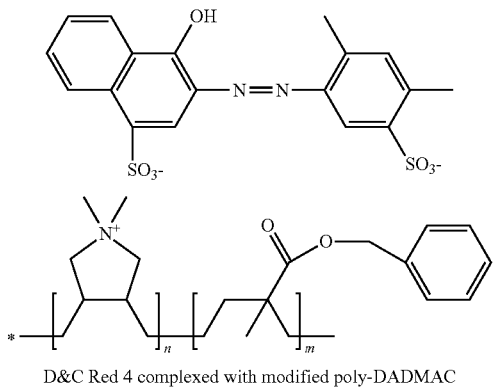

D&C Red 4 complexed with modified poly-DADMAC

A 1-liter reactor equipped with a condenser, a thermometer, a nitrogen inlet, and an overhead agitator is charged with DADMAC monomer (453.8 g, 66% assay), benzyl methacrylate (15.8 g), deionized water (57.4 g) and Na$_4$EDTA (0.15 g, 20% assay). The polymerization mixture is purged with nitrogen and heated with agitation to a temperature of 90 C. An aqueous solution containing ammonium persulfate (APS, 5.1 g) is slowly fed to the reactor over 190 minutes. The reaction temperature is allowed to increase to above 100 C and then maintained at reflux temperature (100-110 C) during the APS feed period. After the APS feed, the reaction temperature is lowered to and held at 95 C for about 30 minutes. At this point, an aqueous solution containing sodium metabisufite (MBS, 5.6 g) is added over 30 minutes. The reactor content temperature is held at 95 C for another 30 minutes to complete the polymerization (above 99% conversion). The polymer solution is diluted with sufficient deionized water to achieve a concentration of about 35% solids and cooled to room temperature. Total monomer conversion is measured to be above 99.5%. The final product has a Brookfield viscosity of 15,440 cps at 25° C. and 36.3% polymer solids.

According to the dye complexation procedure of Instant Example 1, the instant dye-polymer complex is formed between D&C Red 4 and the copolymer of DADMAC and benzyl methacrylate.

EXAMPLE 7

D&C Red 4 Dye Complex with
Co-polyDADMAC-copolybutylmethacrylate

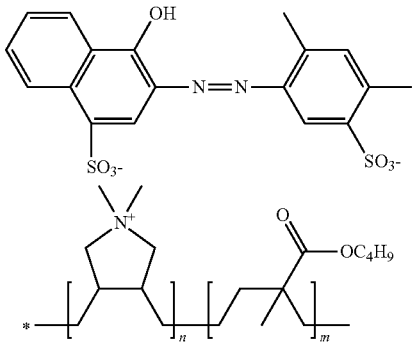

D&C Red 4 complexed with modified poly-DADMAC

A 1-liter reactor equipped with a condenser, a thermometer, a nitrogen inlet, and an overhead agitator is charged with DADMAC monomer (453.8 g, 66% assay, Aldrich), butyl methacrylate (15.8 g, Aldrich), deionized water (57.4 g) and Na$_4$EDTA (0.15 g, 20% assay, Aldrich). The polymerization mixture is purged with nitrogen and heated with agitation to a temperature of 90 C. An aqueous solution containing ammonium persulfate (APS, 5.1 g, Aldrich) is slowly fed to the reactor over 190 minutes. The reaction temperature is allowed to increase to above 100 C and then maintained at reflux temperature (100-110 C) during the APS feed period. After the APS feed, the reaction temperature is lowered to and held at 95 C for about 30 minutes. At this point, an aqueous solution containing sodium metabisufite (MBS, 5.6 g, Aldrich) is added over 30 minutes. The reactor content temperature is held at 95 C for another 30 minutes to complete the polymerization (above 99% conversion). The polymer solution is diluted with sufficient deionized water to achieve a concentration of about 35% solids and cooled to room temperature. Total monomer conversion is measured to be above 99.5%. The final product has a Brookfield viscosity of 15,200 cps at 25° C. and 35.2% polymer solids.

According to the dye complexation procedure of Instant Example 1, the instant dye-polymer complex is formed between D&C Red 4 and the copolymer of DADMAC and butyl methacrylate.

EXAMPLE 8

D&C Red 4 Dye Complex with
Co-polyDADMAC-copolyethoxylated nonylphenol
acrylate

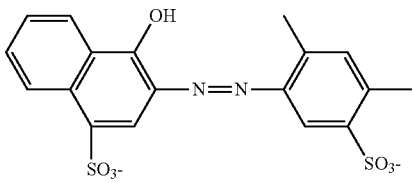

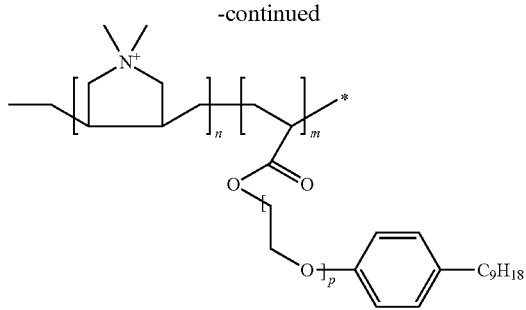

D&C Red 4 complexed with modified poly-DADMAC

A 1-liter reactor equipped with a condenser, a thermometer, a nitrogen inlet, and an overhead agitator is charged with DADMAC monomer (453.8 g, 66% assay based on weight, Aldrich), ethyoxlated nonylphenol acrylate (15.8 g, SR504, Sartomer), deionized water (57.4 g) and Na$_4$EDTA (0.15 g, 20% assay, Aldrich). The polymerization mixture is purged with nitrogen and heated with agitation to a temperature of 90 C. An aqueous solution containing ammonium persulfate (APS, 5.1 g, Aldrich) is slowly fed to the reactor over 190 minutes. The reaction temperature is allowed to increase to above 100 C and then maintained at reflux temperature (100-110 C) during the APS feed period. After the APS feed, the reaction temperature is lowered to and held at 95 C for about 30 minutes. At this point, an aqueous solution containing sodium metabisufite (MBS, 5.6 g, Aldrich) is added over 30 minutes. The reactor content temperature is held at 95 C for another 30 minutes to complete the polymerization (above 99% conversion). The polymer solution is diluted with sufficient deionized water to achieve a concentration of about 35% solids and cooled to room temperature. Total monomer conversion is measured to be above 99.5%. The final product has a Brookfield viscosity of 19,500 cps at 25° C. and 34.8% polymer solids.

According to the dye complexation procedure of Instant Example 1, the instant dye-polymer complex is formed between D&C Red 4 and the copolymer of DADMAC and ethoxylated nonylphenol acrylate.

EXAMPLE 9

D&C Red 4 Dye Complex with Hydrophobically Crosslinked poly-DADMAC

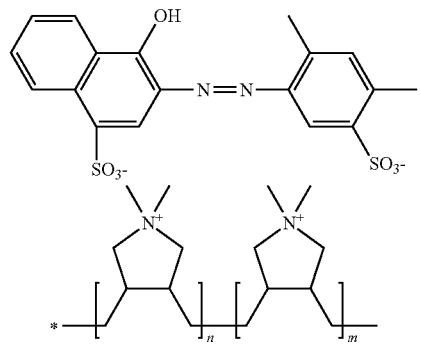

D&C Red 4 complexed with hydrophobically crosslinked poly-DADMAC

To a suitable reactor kettle equipped with a condenser, a thermometer, a nitrogen inlet, and an overhead agitator is charged with DADMAC aqueous solution (452.51 g, 65.9% assay by weight, Aldrich), diallylamine (1.809 g, >99% assay by weight, Aldrich), concentrated hydrochloric acid (1.62 g, 37% assay by weight), Na$_4$EDTA (0.6 g, 20% assay by weight, Aldrich), and deionized water (96.81 g). The polymerization mixture is purged with nitrogen and heated with agitation to a temperature of 80 C. An aqueous solution containing ammonium persulfate (3.5 g, APS, Aldrich) dissolved in deionized water (66.5 g) is slowly fed into the reactor over 280 minutes. The reaction temperature is allowed to increase to above 90 C and then maintained at 90-100 C during the APS feed period. After the APS feed, the reaction mixture is diluted with deionized water to a concentration of about 35% solids and held at 90 C for about thirty minutes. At this point, an aqueous solution containing sodium metabisufite (MBS, 3.00 g) dissolved in deionized water (12 g) is added over ten minutes. The reactor contents are held at 90 C for another 30 minutes to complete the polymerization. The polymer solution is diluted with sufficient deionized water to about 30% solids. The final product (12zs79B) has a Brookfield viscosity of 1,600 cps at 25° C. and a pH of 3.

In a 1-liter reactor fitted with a mechanical stirrer, addition funnel and condenser is charged with 250.00 grams of the above synthesized polymer (12zs79B) and deionized water (143.6 g). The reactor content is heated to 72° C. with agitation and adjusted with NaOH aqueous solution to a pH of 10. After the pH adjustment, diglycidyl ether bisphenol A (0.89 g, DGEBA, average MW=348) is added into the reactor. The crosslinking reaction is allowed to proceed at 70° C. until little to no increase in viscosity is observed. After the reaction, the polymer solution is diluted with deionized water to 20% solids and adjusted with concentrated HCl solution to a pH of 4.5. The final product is a gel-free white-emulsion-like polymer solution with a Brookfield viscosity of 35,200 cps at 25 C.

According to the dye complexation procedure of Instant Example 1, the instant dye-polymer complex is formed between D&C Red 4 and the hydrophobically crosslinked polymer of DADMAC.

EXAMPLE 10

In-Situ Formed Beads of FD&C Blue 1 Dye Complex with Linear poly-DADMAC

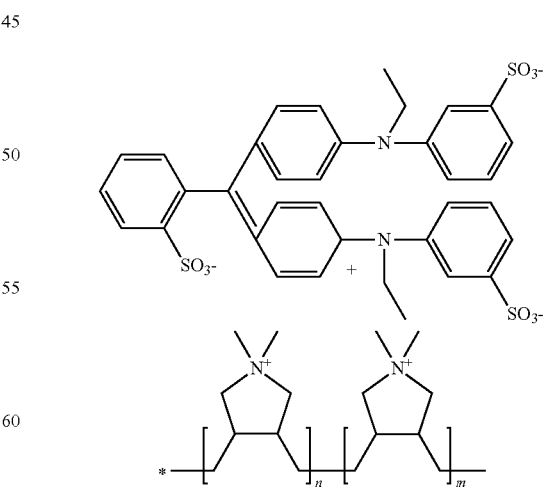

FD&C Blue 1 complexed with linear poly-DADMAC

A 0.5-liter reactor equipped with a condenser, a thermometer, a nitrogen inlet, and an overhead agitator is charged with Naphthol Spirits oil (240 g, CITGO) and 1.2 g of polymer stabilizer (a copolymer of methyl methacrylate and acrylic acid). To the reactor is added an agitated monomer and dye aqueous solution consisting of DADMAC (206.2 g, 66.5% assay by weight, Aldrich), Na$_4$EDTA (0.012 g, 20% assay by weight, Aldrich), 2,2'-azobis(2-amidinopropane) dihydrochloride, (6.61 g, V50, Wako, 41% assay by weight) and FD&C blue #1 dye (1.43 g, Aldrich). The reactor content is purged with nitrogen and heated to and held at 40 C for one hour, 50 C for two hours, and 60 C for two and half hours. An aliquot of reaction is taken and the viscosity is determined to be 3200 cps at 20% solids at 25 C. At this point, the reaction mixture is heated to reflux temperature at 82+/-2.0 C for about 2 hours and the water is azeotropically removed. The reaction mixture is cooled and filtered. The filtered cake was further dried in an oven at 90 C for 3 hours. The final product consists of free flowing beads of intense dark blue color with particle size of about 300 micrometers.

The FD&C blue #1 dye is soluble in polar solvents such as isopropanol. The instant beads of the dye-polymer complex with polyDADMC are insoluble in isopropanol and show no color bleeding (color dispersal) to the liquid phase.

EXAMPLE 11

Beads of FD&C Blue 1 Dye Complex with Crosslinked poly-DADMAC Hydrogel Beads

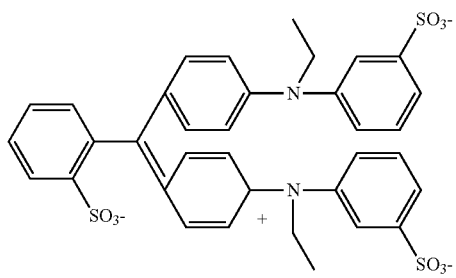

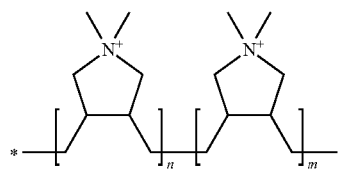

FD&C Blue 1 complexed with crosslinked poly-DADMAC

A 0.5-liter reactor equipped with a condenser, a thermometer, a nitrogen inlet, and an overhead agitator is charged with Naphthol Spirits oil (240 g, CITGO) and 1.2 g of polymer stabilizer (a copolymer of methyl methacrylate and acrylic acid). To the reactor is added an agitated aqueous monomer solution consisting of DADMAC (206.2 g, 66.5% assay by weight, Aldrich), Na$_4$EDTA (0.012 g, 20% assay by weight, Aldrich), 2,2'-azobis(2-amidinopropane) dihydrochloride, (6.61 g, V50, Wako, 41% assay by weight) and methylenebisacrylamide (2.7 g, Aldrich). The reactor content is purged with nitrogen and heated to and held at 40 C for one hour, 50 C for two hours, and 60 C for two and half hours. At this point, the reaction mixture is heated to reflux temperature at 82+/-2.0 C for about 2 hours and the water is azeotropically removed. The reaction mixture is cooled and filtered. The filtered cake was further dried in an oven at 90 C for 3 hours. The final product consists of free flowing beads with a particle size of about 300 micrometers.

A FD&C blue #1 dye aqueous solution (12.4 g, 6% assay by weight, Aldrich) is added to crosslinked poly-DADMAC beads, as prepared above, (3 g on a dry basis) in deionized water (124.7 g) with agitation. After standing overnight for the completion of the dye complexing process, the beads have shrunk and become dark blue in color. The aqueous phase is very light blue in color. The pigment bead slurry is filtered and washed thrice with copious amounts of deionized water and twice with acetone. After being dried in a 100 C oven for 24 hours, the product is ground to a powder using a SPEX freezer mill to yield about 4.3 g of blue dye-polymer complex which is insoluble in organic solvent and water.

EXAMPLE 12

Beads of FD&C Red 2 Dye Complex with Crosslinked poly-DADMAC Hydrogel Beads

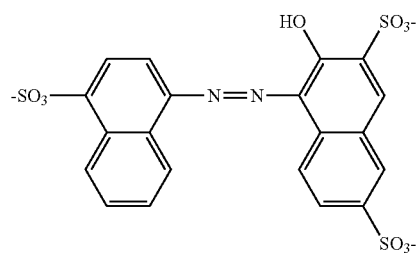

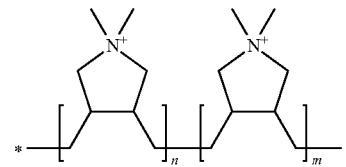

FD&C Red 2 complexed with crosslinked poly-DADMAC

A FD&C Red 2 dye aqueous solution (10 g, 5% assay by weight, Aldrich) is added to crosslinked poly-DADMAC beads, as prepared in Instant Example 11, (1.3 g on a dry basis) in deionized water (49.7 g) with agitation. After standing overnight for the completion of the dye complexing process, the beads have shrunk and become dark red in color. The aqueous phase is very light red in color. The pigment bead slurry is filtered and washed thrice with copious amounts of deionized water. After being dried in an 80 C oven for 5 hours, the product is ground to a powder using a SPEX freezer mill to yield about 1.5 g of red dye-polymer complex which is insoluble in organic solvent and water.

EXAMPLE 13

Beads of FD&C Red 6 Dye Complex with Crosslinked poly-DADMAC

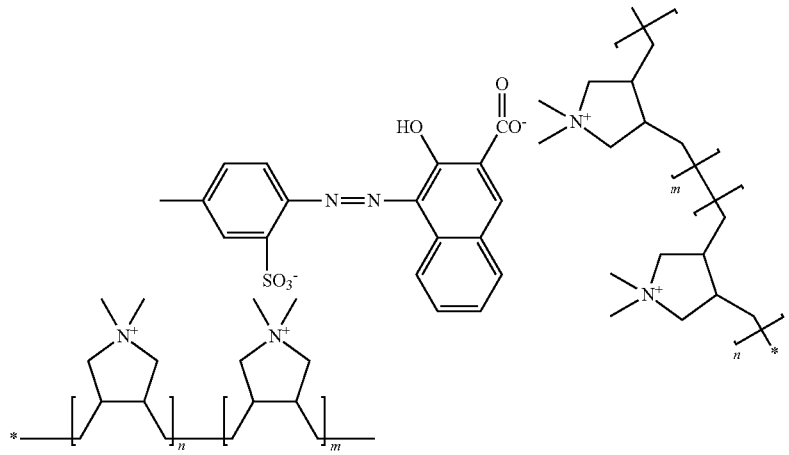

D&C Red 6 complexed with crosslinked polyDADMAC

A FD&C Red 6 dye aqueous solution (5.4 g, 0.3% assay by weight, Ciba CALISHA) is added to crosslinked poly-DAD-MAC beads (0.2 g on a dry basis) in deionized water (3 g) with agitation. After standing overnight for the completion of the dye complexing process, the hydrogel beads have shrunk and become dark red in color. The aqueous phase is very light red in color. The bead slurry is filtered and washed thrice with copious amounts of deionized water. After being dried in an 80 C oven for 5 hours, the product is ground to a powder using a SPEX freezer mill to yield about 0.2 g of red dye-polymer complex which is insoluble in organic solvent and water.

EXAMPLE 14

FD&C Blue 1 Dye Complex with polyepiamine

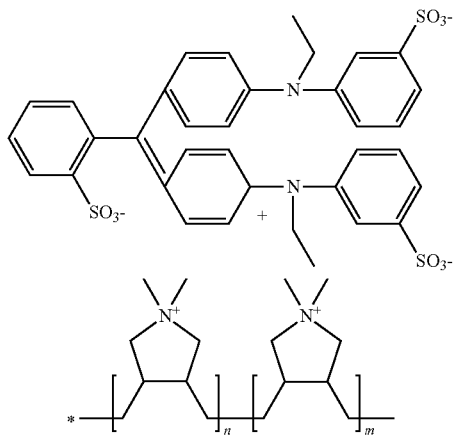

FD&C Blue 1 complexed with crosslinked poly-DADMAC

Polyepiamine (6.55 g, 100% solids, molecular weight and other data is located in Instant Example 1) is added to a FD&C blue #1 aqueous solution (32.5 g, 6% assay by weight) with agitation. Soft sticky coagulum precipitates out. The water insoluble precipitate is collected and washed with copious amounts of deionized water until little to no blue color was seen in the filtrate. After drying in an 80 C oven for 20 hrs, the desired solid product (1 g) is obtained as a lustrous violet dye-polymer complex with a metal shining appearance.

EXAMPLE 15

D&C Red 4 Dye Complex with a Modified DADMAC/Diallylamine Copolymer

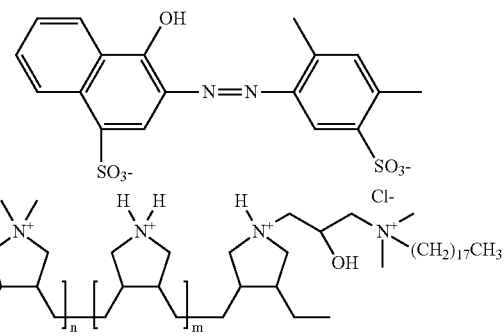

D&C Red 4 complexed with a modified copolymer of DADMAC/DAA

In 1 L reactor equipped with the necessary auxiliary equipment, DADMAC (65 wt %, 260 g, Aldrich), diallylamine (97%, 19.4 g, Aldrich, DAA) and $Na_4EDTA$ (0.4 g, dissolved in 2.95 g of deionized water, Aldrich) are added. To the mixture, concentrated hydrochloric acid (19.1, 37% assay by weight) and deionized water (24 g) are added. The solution is heated to 92 C and ammonium persulfate initiator (3.3 g, dissolved in 18.5 g of deionized water, Aldrich) is added at a rate of 0.05 mL/min. During the polymerization, water is added if the solution viscosity becomes too high. After addition of the initiator, the solution is further stirred for an additional one hour. Sodium metabisulfite (6 g dissolved in 24 g deionized water, Aldrich) is then added at 0.5 mL/min and the solution is further stirred for another hour, after which water is added to bring the solid content to about 40% by weight. The molecular weight of the instant copolymer is 315,000 Daltons.

An aliquot of the DADMAC/DAA copolymer described above (100 g, 40 wt % solids content, 10 wt % DAA) is diluted by adding deionized water (200 g). An aqueous solution of NaOH (2 g, dissolved in 10 g of deionized water, 50 mmol) is added. The mixture is heated to 70 C with stirring. To this solution, Quab 426 (Degussa, 40 wt % in propane-1,2-diol/water, 4.6 g, 4.3 mmol) is added. The mixture is stirred for ten hours at this temperature. Water is added during the reaction if the solution viscosity becomes too high and agitation becomes difficult. The solid content of final product is 11.8 wt %.

Preparation of the Complex. A one % by weight aqueous solution of the copolymer above (30 mL) is added gradually over 10 minutes to a one % by weight aqueous solution of Red D&C #4 Dye (Puricolor, Ciba Specialty Chemicals, 30 mL) with rapid stirring. A deep red precipitate is formed throughout the addition. The mixture is stirred for an additional 10 minutes, then let stand so that all solids settle to the bottom. The pale orange/pink solution is decanted from the deep red solid. The solid is then washed with deionized water three times by stirring in 10 mL for 10 minutes each and decanting as above. The solid was then air dried for two days and collected. The desired product is obtained (0.41 g) as a brilliant red dye-polymer complex.

Evaluation of Color Bleed from Complex. Approximately 50 mg of the isolated solid dye-polymer complex is placed in 10 mL of deionized water and shaken briefly. It is then allowed to stand in a sealed vial for one week. Visual evaluation of the water indicates only a very faint orange color of the aqueous layer indicating little to no bleed into the aqueous layer.

EXAMPLE 16

Aqueous Test Formulation

An aqueous based test formulation is prepared as follows:

| sodium laureth sulfate (30%, TEXAPON NSO, Cognis) | 30% |
|---|---|
| cocamidopropylbetaine (30%, DEHYTON K, Cognis) | 10% |
| Instant dye-polymer complex | 0.001% |
| benzotriazole UV Absorber* | 0.05% |
| citric acid (10% aqueous solution) | to pH 6 |
| deionized water | to 100% |

*UV absorber is 3-(2H-benzotriazol-2-yl)-4-hydroxy-5-(1-methylpropyl)-benzenesulfonic acid monosodium salt.

About 20 mL of each of the aqueous test formulations is placed in a borosilicate glass bottle. The glass bottles are exposed in an Atlas Ci-65 Xenon arc WeatherOmeter, AATCC Test Method 16. Color measurements are performed on a Hunter Ultrascan XE spectrophotometer. Delta L, a and b values are the difference between the initial values and the values at each interval. It is seen that the dye-polymer complexs of the present invention provide excellent color stability in personal care products.

EXAMPLE 17

Aqueous Test Formulation

An aqueous based test formulation is prepared as follows:

| sodium laureth sulfate (30%, TEXAPON NSO, Cognis) | 30% |
|---|---|
| cocamidopropylbetaine (30%, DEHYTON K, Cognis) | 10% |
| instant dye-polymer complex | 0.001% |
| UV absorber | 0.05% |
| citric acid (10% aqueous solution) | to pH 6 |
| deionized water | to 100% |

*UV absorber is an s-triazine derivative.

About 20 mL of each of the aqueous test formulations is placed in a borosilicate glass bottle. The glass bottles are exposed in an Atlas Ci-65 Xenon arc WeatherOmeter, AATCC Test Method 16, option E. Color measurements are performed on a Hunter Ultrascan XE spectrophotometer. Delta L, a and b values are the difference between the initial values and the values at each interval. It is seen that the dye-polymer complexes of the present invention provide excellent color stability in personal care products.

EXAMPLE 18

Aqueous Test Formulation

An aqueous based test formulation is prepared as follows:

| sodium laureth sulfate (30%, TEXAPON NSO, Cognis) | 30% |
|---|---|
| cocamidopropylbetaine (30%, DEHYTON K, Cognis) | 10% |
| instant dye-polymer complex | 0.001% |
| UV absorber | 0.05% |
| citric acid (10% aqueous solution) | to pH 6 |
| deionized water | to 100% |

*UV absorber is a benzophenone derivative.

About 20 mL of each of the aqueous test formulations is placed in a borosilicate glass bottle. The glass bottles are exposed in an Atlas Ci-65 Xenon arc WeatherOmeter, AATCC Test Method 16. Color measurements are performed on a Hunter Ultrascan XE spectrophotometer. Delta L, a and b values are the difference between the initial values and the values at each interval. It is seen that the dye-polymer complexes of the present invention provide excellent color stability in personal care products.

EXAMPLE 19

Aqueous Test Formulations

An aqueous based test formulation is prepared as follows:

| sodium laureth sulfate (30%, TEXAPON NSO, Cognis) | 30% |
|---|---|
| cocamidopropylbetaine (30%, DEHYTON K, Cognis) | 10% |
| instant dye-polymer complex | 0.001% |
| UV absorber* | 0.05% |
| instant stabilizer** | 0.10% |
| citric acid (10% aqueous solution) | to pH 6 |
| deionized water | to 100% |

*UV absorber is 3-(2H-benzotriazol-2-yl)-4-hydroxy-5-(1-methylpropyl)-benzenesulfonic acid monosodium salt.
Instant stabilizer** is 1-oxyl-2,2,6,6-tetramethyl-4- hydroxypiperidine which is disclosed in WO2003103622, the publication of U.S. patent application Ser. No. 60/377,381, filed May 2, 2002, incorporated herein by reference.

About 20 mL of each of the aqueous test formulations is placed in a borosilicate glass bottle. The glass bottles are also exposed to accelerated fluorescent lighting, Philips, 40 Watt, Daylight Deluxe (D65), full exposure to light. Color measurements are performed on a Hunter Ultrascan XE spectrophotometer. Delta L, a and b values are the difference between the initial values and the values at each interval. It is seen that the dye-polymer complexes of the present invention provide excellent color stability in personal care products.

EXAMPLE 20

Moisturizer Cream

The components of phase A are thoroughly mixed in a homogenizer for 10 min at 75-80° C. The water phase B, likewise heated to 75-80° C. beforehand, is slowly added and the mixture is homogenized for 1 min. The mixture is cooled, with stirring, to 40° C. and then phases C and E are added and the mixture is homogenized for 1 min. Subsequently, phase D is added and the mixture is homogenized for ½ min and cooled, with stirring, to room temperature.

| Phase | Ingredients | (w/w) % |
|---|---|---|
| A | passionflower oil | 8 |
|   | glyceryl dioleate | 4 |
|   | dicapryl ether | 4 |
|   | Isopropylisostearate | 4 |
|   | dye-polymer complex | 0.05 |
| B | water, demin. | ad. 100 |
|   | EDTA | 0.1 |
| C | Carbomer | 0.15 |
| D | sodium hydroxide | 10% |
|   | 1-oxyl-2,2,6,6-tetramethyl-4-hydroxypiperidine | 0.20 |
| E | perfume; preservative | q.s. |

It is seen that the dye-polymer complexes of the present invention provide excellent color stability in personal care products.

EXAMPLE 21

Hair Styling Spray

The hydroxypropyl cellulose is first predissolved in half of the alcohol (Vortex mixer) and is charged with the aminomethylpropanol. The other components—with the exception of the acrylate resin—are dissolved in alcohol and this solution is added, with stirring, to the hydroxypropyl cellulose. Subsequently, the acrylate resin is added and stirred until completely dissolved. The UV absorber used is, for example, benzophenone-4 is 5-benzoyl-4-hydroxy-2-methoxybenzenesulfonic acid, sodium salt.

| Ingredients | (w/w) % |
|---|---|
| alcohol, anhydrous | 96.21 |
| octylacrylamide/acrylate/butylaminoethylmethacrylate copolymer | 2.52 |

-continued

| Ingredients | (w/w) % |
|---|---|
| hydroxypropyl cellulose | 0.51 |
| aminomethylpropanol (95%) | 0.46 |
| dye-polymer complex | 0.05 |
| UV absorber | 0.05 |
| perfume oil | 0.20 |

Excellent results are achieved for this example of a hair styling spray formulation.

EXAMPLE 22

Shampoo for Oily Hair

The components listed below are mixed, with stirring, at room temperature until they are completely dissolved. The pH is 6.5. The UV absorber is, for example, 2-(2-hydroxy-3-dodecyl-5-methylphenyl)-2H-benzotriazole.

| Ingredients | (w/w) % |
|---|---|
| sodium myreth sulfate | 50.00 |
| TEA abietoyl collagen hydrolysate | 3.50 |
| laureth-3 | 3.00 |
| colorant (D&C Red No. 33) | 0.20 |
| dye-polymer complex | 0.05 |
| UV absorber | 0.15 |
| phosphonomethylchitosan, sodium salt | 0.01 |
| perfume oil | 0.10 |
| water | ad. 100 |

Excellent results are achieved for this example of a shampoo composition for oily hair.

EXAMPLE 23

Dye-Polymer Complex Particle Incorporation into Nail Lacquers

A dye-polymer complex according to the instant invention and a pearlescent pigment are respectively incorporated into a nail lacquer base at 5% by weight, based on particle weight, and stirring constantly with a propeller-type stirrer. After incorporation, both the nail lacquers are let down.

Visual assessment shows that the modified pearlescent pigment according to the instant invention exhibits significantly more gloss than the untreated sample.

EXAMPLE 24

Pressed Powder Eye-Shadow

| INCI | Tradename | Supplier | Concentration |
|---|---|---|---|
| Talc | Talc Micro Ace P-2 | Presperse, Inc. | 41.50 |
| Zinc Stearate | Zinc Stearate | Witco Corp. | 5.00 |
| PTFE | Microslip 519 | Presperse, Inc. | 4.00 |
| Nylon-12 | Nylon-12 | Lipo Chemicals | 4.00 |
| Mica | Sericite PHN | Presperse, Inc. | 10.00 |
| Ultramarines | Ultramarine Blue | Sensient Technologies | 5.00 |
| Manganese Violet | Manganese Violet | Sensient Technologies | 10.00 |
| Ferric Ferrocyanide | Ferric Ferrocyanide | Sensient Technologies | 0.50 |
| Squalane | Squalane | Lipo Chemicals | 5.00 |
| Phenoxyethanol (and) Caprylyl Glycol (and) Sorbic Acid | Optiphen Plus | International Specialty Products | 1.00 |
| | Dye-Polymer Complex | | 14.00 |

All the ingredients are weighed in the initial phase and brought together in an osterizer or suitable grinder. When the initial phase is uniform and free of pigment specks, the binder phase is slowly added to the powder and hand mixed until the binder is completely dispersed and homogeneous. The batch is osterized again to make sure that the powder is completely wet out and the batch is uniform. The instant modified pigment is added and slowly blended to make sure it is completely uniform in the batch. Care is taken not to over grind the modified pearlescent pigment. When complete, the entire blended contents are stored in airtight containers until needed. A small amount of the batch is pressed into eye shadow pans.

EXAMPLE 25

O/W Foundation Makeup

| INCI | Tradename | Supplier | Concentration |
|---|---|---|---|
| Deionized Water | Deionized Water | | 63.75 |
| Cellulose Gum | CMC 7H3SF Gum | Hercules | 0.30 |
| Magnesium Aluminum Silicate | Veegum Ultra | RT Vanderbilt | 0.35 |
| Butylene Glycol | Butylene Glycol | Lipo Chemicals | 4.50 |
| Lecithin | Alcolec S | American Lecithin | 0.20 |
| Triethanolamine | Triethanolamine 99% | Lipo Chemicals | 1.20 |
| Titanium Dioxide | Titanium Dioxide | Kronos | 8.00 |
| Iron Oxides | Red Iron Oxide | Sun Chemical | 0.40 |
| Iron Oxides | Yellow Iron Oxide | Sun Chemical | 0.80 |
| Iron Oxides | Black Iron Oxide | Sun Chemical | 0.10 |
| Methyl Paraben | Methyl Paraben | Lipo Chemicals | 0.20 |
| Calcium Aluminum Borosilicate | Luxsil | Potters Industries | 2.00 |
| Isoeicosane | Permethyl 102A | Presperse Inc. | 10.00 |
| Isostearic Acid | Isostearic Acid | Lipo Chemicals | 1.00 |
| Stearic Acid | Stearic Acid | Lipo Chemicals | 2.50 |
| Glyceryl monostearate | LIPO GMS 450 | Lipo Chemicals | 1.50 |
| Tridecyl Trimellitate | Liponate TDTM | Lipo Chemicals | 1.00 |
| Glyceryl monostearate | LIPO GMS 470 | Lipo Chemicals | 1.00 |
| Propyl Paraben | Propyl Paraben | Lipo Chemicals | 0.20 |
| | Dye-Polymer Complex | | 1.00 |

Weigh water phase ingredients in a suitable vessel and begin mixing to wet out the gums. Pregrind the color phase in an osterizer or equivalent grinder. When the gums are hydrated and the phase is uniform, add the ground color phase to the water phase and mix until all the color is dispersed. Begin to heat the water phase ingredients to 75° C. with good mixing. In a separate vessel, weight the oil phase ingredients and begin heating to 75-80° C. When both phases are uniform and at the proper temperatures, slowly add the oil phase to the water phase with continuous mixing. Mix the batch for 15 minutes and then begin cooling to 25° C. At 25° C. remove the batch and store in airtight containers until ready for filling.

EXAMPLE 26

Moisturizer

| Phase | INCI Name | Trade Name | Supplier | Parts |
|---|---|---|---|---|
| A | Deionized Water | DI Water | N/A | Qs to 100 |
| A | Sclerotium Gum | Tinocare GL | Ciba SC | 1.00 |
| A | | Salcare SC 96 | Ciba SC | 3.00 |
| B | PPG-3 Benzyl Ether Myristate | Crodamol STS | Croda | 5.00 |
| B | Cetearyl Isononanoate | Cetiol SN | Cognis | 5.00 |
| B | | Dye-Polymer Complex | Ciba SC | 0.50 |
| C | Phenoxyethanol and Caprylyl Glycol and Sorbic Acid | Optiphen Plus | ISP | 0.50 |
| C | Fragrance | Fragrance | N/A | 0.50 |

Combine A ingredients and heat to 80° C. Add B to A

Combine C ingredients and heat to 80° C. Add C to A & B with continuous mixing for 10-15 minutes. Cool to 25° C. with good mixing. Store in airtight containers until ready for filling. Fill at room temperature.

EXAMPLE 27

Pearlized Lipstick

| INCI Name | Trade Name | Supplier | Parts |
|---|---|---|---|
| White Beeswax | Beeswax, white | Kahl & Co | 8.00 |
| Candelilla Wax | Candelilla Wax | Rita Corp. | 4.50 |
| Carnauba Wax | Carnauba Wax #1 | Strahl & Pitsch | 6.00 |
| Isoeicosane | Permethyl 102A | Presperse | 6.00 |
| Polyisobutene | Permethyl 104A | Presperse | 3.50 |
| Isopropyl Palmitate | Crodamol IPP | Croda | 11.00 |
| Tridecyl Trimellitate | Liponate TDTM | Lipo Chemicals | 10.00 |
| Caprylic/Capric Triglyceride | Liponate GC | Lipo Chemicals | 4.00 |
| Ethylhexyl Palmitate | Ceraphyl 368 | ISP | 8.35 |
| Propyl Paraben | Nipasol M | Clariant | 0.10 |
| Pentaerythrityl Tetra-di-t-butyl Hydroxyhydrocinnamate | Tinogard TT | Ciba SC | 0.05 |
| Castor Oil | Castor Oil USP | Sud Chemie | To 100 |
| Red Iron Oxide, Yellow iron Oxide, black Iron Oxide | Unipure Red LC831 Unipure Yellow LC181 Unipure Black LC989 | Sensient | q.s. |
| | Dye-Polymer Complex | | 10.00 |

Melt all solid waxes at 70-80 Degrees Celsius and add rest of ingredients under stirring once the waxes are melted. When homogeneous poor into lipstick molts and let cool down to room temperature. Remove lipsticks from molds.

EXAMPLE 28

Lipstick

| Phase | INCI Name | Trade Name | Supplier | Parts |
|---|---|---|---|---|
| A | Castor Oil | Lipovol CO | Lipo | 33.25 |
| A | Triethylhexanoin | Schercemol GTO | Scher | 7.50 |
| A | Triisostearyl Trilinoleate | Schercemol TIST | Scher | 15.00 |
| A | Triisostearyl Citrate | Schercemol TISC | Scher | 17.50 |
| A | *Euphorbia Cerifera* (Candelilla) Wax | Refined Candelilla Wax Prills | Ross Waxes | 7.00 |
| A | *Copernicia Cerifera* (Carnauba) Wax | Yellow Carnuba Wax Flakes | Ross Waxes | 1.80 |
| A | Ozokerite | White Ozokerite Wax 77W | Ross Waxes | 1.80 |
| A | Microcyrstalline Wax | Microcrystalline Wax 1275W | Ross Waxes | 3.50 |
| A | Hydroxylated Lanolin | Ritahydrox | Rita | 1.00 |
| A | Methylparaben | Nipagin M | Clariant | 0.20 |
| A | Propylparaben | Nipasol M | Clariant | 0.10 |
| B | Iron Oxides | Modified Red Pigment (according to instant invention) | Ciba Specialty Chemicals | 5.70 |
| B | Iron Oxides | Modified Yellow Pigment (according to instant invention) | Ciba Specialty Chemicals | 1.10 |
| B | Ultramarines | Modified Blue Pigment (according to instant invention) | Ciba Specialty Chemicals | 0.20 |
| B | | Dye-Polymer Complex | Ciba Specialty Chemicals | 4.35 |
| | | | Total | 100.00 |

Procedure:
Phase A is combined, heated between 90-105° C., and mixed until uniform. Phase B is then added with stirring until homogenous. The temperature is maintained above 70° C. as the lipstick is poured into the mold.

EXAMPLE 29

Medium Protection Sunscreen

| Phase | INCI Name | Trade name | Supplier | Parts |
|---|---|---|---|---|
| A | Deionized Water | DI Water | N/A | 84.86 |
| A | Propylene Glycol (and) Diazolidinyl Urea (and) Methylparaben (and) Propylparaben | Germaben II | ISP | 1.00 |
| A | Aloe Barbadensis Leaf Juice | Aloe Gel 1:1 Natural | Tri-K Industries | 1.00 |
| A | Propylene Glycol | Propylene Glycol | Dow Chemical | 2.50 |
| A | Butylene Glycol (and) Water (and) Juglans Nigra (Black Walnut) Shell Extract | Actiphyte of Black Walnut Hull | Active Organics | 0.04 |
| A | Ethyhexyl Salicylate | Escalol 587 | ISP | 5.00 |
| A | Ethylhexyl Methoxycinnamate | Escalol 557 | ISP | 3.00 |
| B | Sodium Acrylates Copolymer (and) Paraffinum Liquidum (and) PPG-1 Trideceth-6 | Ciba ® SALCARE ® SC91 | Ciba Specialty Chemicals | 2.00 |
| C | Iron Oxides | Modified Red Pigment (according to instant invention) | Ciba Specialty Chemicals | 0.20 |
| C | | Dye-Polymer Complex | Ciba Specialty Chemicals | 0.10 |
| D | Fragrance | Flowers in the mist | Belle Aire Fragrances | 0.30 |
| | | | Total | 100.00 |

Procedures:

In an appropriate vessel add Part A and start moderate agitation.

Add part B and mix until uniform.

Add Part C, than part D and mix until well blended.

EXAMPLE 30

Talc Free Loose Face Powder

| Phase | INCI Name | Trade Name | Supplier | Parts |
|---|---|---|---|---|
| A | Mica | Sericite PHN | Presperse | 81.45 |
| A | Polymethyl Methacrylate | Ganzpearl GM-0600W | Presperse | 5.00 |
| A | Synthetic Wax and Corn Gluten Protein | Microease 110XF | Presperse | 2.00 |

-continued

| Phase | INCI Name | Trade Name | Supplier | Parts |
|---|---|---|---|---|
| A | Titanium Dioxide | Titanium Dioxide 3228 | Whittaker, Clark & Daniels | 5.00 |
| A | Methylparaben | Nipagin M | Clariant | 0.20 |
| A | Propylparaben | Nipasol M | Clariant | 0.10 |
| A | Imidazolidinyl Urea | Germall 115 | ISP | 0.25 |
| B | | Dye-Polymer Complex | Ciba Specialty Chemicals | 1.00 |
| | | | Total | 100.00 |

Procedure:

Mill together A until fully dispersed. Add B to A and blend until uniform.

EXAMPLE 31

Oil in Water Facial Foundation

| Phase | INCI Name | Trade Name | Supplier | Parts |
|---|---|---|---|---|
| A | Deionized water | DI Water | N/A | 53.94 |
| A | 10% KOH solution | 10% KOH solution | N/A | 1.30 |
| A | PEG-12 Dimethicone | DC 193 Surfactant | Dow Corning | 0.10 |
| A | Talc | Talc | Whittaker, Clark & Daniels | 0.72 |
| B | 1,3-Butylene Glycol | Jeechem BUGL | Jeen Int. | 4.00 |
| B | Magnesium Aluminum Silicate | Veegum Granules | R. T. Vanderbilt | 1.00 |
| C | 1,3-Butylene Glycol | Jeechem BUGL | Jeen Int. | 2.00 |
| C | Cellulose Gum | CMC 7MF | Hercules | 0.12 |

-continued

| Phase | INCI Name | Trade Name | Supplier | Parts |
|---|---|---|---|---|
| C | Methylparaben | Nipagin M | Clariant | 0.02 |
| D | Di-PPG-3 Myristyl Ether Adipate | Cromollient DP3-A | Croda | 14.00 |
| D | Diethyl Hexyl Maleate | Pelemol DOM | Phoenix | 4.00 |
| D | Steareth-10 | Lipocol S-10 | Lipo | 2.00 |
| D | Steareth-2 | Lipocol S-2 | Lipo | 0.50 |
| D | Cetyl Alcohol | Crodacol C-95 NF | Croda | 0.62 |
| D | Dicetyl Phosphate and Ceteth-10 Phosphate and Ceteryl Alcohol | Crodafos CES | Croda | 4.00 |
| D | Propyl Paraben | Nipasol M | Clariant | 0.10 |
| E | Titanium Dioxide | White Pigment | Ciba Specialty Chemicals | 7.50 |
| E |  | Dye-Polymer Complex | Ciba Specialty Chemicals | 1.20 |
| E | Ultramarine | Blue Pigment | Ciba Specialty Chemicals | 0.20 |
| F | DMDM Hydantoin | Mackstat DM | McIntyre Group | 0.18 |
|  |  |  | Total | 100.00 |

Procedure:

Combine ingredients in phase A using a homogenizer and begin heating to 80° C. Add phase B and C and homogenize for 1 hour. In a separate beaker combine ingredients in phase D, heat to 80° C. and mix until uniform. After all ingredients in phase D have become uniform slowly add to the main phase while continuing to homogenize. Upon complete addition of phase D, homogenize for 15 min at 80° C. then begin cooling the mixture. At 60° C. switch to paddle mixing using moderate agitation. Phase E is added and mixed until homogenous mixture obtained. At 50° C. phase F is added. The mixture is cooled until it reaches room temperature.

EXAMPLE 32

Press Powder Eye Shadow (Red)

| INCI Name | Trade Name | Supplier | Parts |
|---|---|---|---|
| Mica | Sericite PHN | Presperse | 75.60 |
| Zinc Stearate | Zinc Stearate | Witco | 5.00 |

-continued

| INCI Name | Trade Name | Supplier | Parts |
|---|---|---|---|
| Titanium Dioxide | White Pigment | Ciba Specialty Chemicals | 6.00 |
| Iron Oxide | Red Pigment | Ciba Specialty Chemicals | 2.00 |
|  | Dye-Polymer Complex | Ciba Specialty Chemicals | 0.60 |
| Methylparaben | Nipagin M | Clariant | 0.20 |
| Propylparaben | Nipasol M | Clariant | 0.10 |
| Calcium Aluminum Borosilicate | Luxsil | Presperse | 5.00 |
| PEG-4 Diheptanoate | Liponate 2-DH | Lipo | 5.50 |
|  |  | Total | 100.00 |

Procedure:

Combine ingredients and mix well. Heat to 100° C. and press at 2000 psi.

EXAMPLE 33

Nail Enamel

| Phase | INCI Name | Trade name | Supplier | Parts |
|---|---|---|---|---|
| A | Butyl Acetate and Toluene and Nitrocellulose and Tosylamide/Formadlehyde Resin and Isopropyl Alcohol and Dibutyl Phthalate and Ethyl acetate and Camphor and n-Butyl Alcohol and Silica and Quaterinium-18 Hectorite | Suspending Lacquer SLF-2 | Engelhard | 86.00 |
| A | Butyl Acetate (and) Bismuth Oxychloride (and) Nitrocellulose (and) Isopropyl Alcohol (and) Stearylalkonium Hectorite | Biju Ultra UXD | Engelhard | 2.25 |
| A | Mica (and) Titanium Dioxide | Flamenco Ultra Sparkle 4500 | Engelhard | 1.00 |
| A | Colorant | Dye-Polymer Complex (according to instant invention) | Ciba Specialty Chemicals | 1.25 |
| A | Dimethicone | Dow Corning 200 | Dow Corning | 1.00 |

-continued

| Phase | INCI Name | Trade name | Supplier | Parts |
|---|---|---|---|---|
| A | Tosylamide/Epoxy Resin | Lustrabrite S-70 | Telechemische | 4.00 |
| B | Butyl Acetate | Butyl Acetate | Dow Chemical | 1.17 |
| B | Ethyl Acetate | Ethyl Acetate | Dow Chemical | 0.42 |
| B | Toluene | Toluene | Shell | 1.66 |
|   |   |   | Total | 100.00 |

Procedure:

Combine phase A and mix until uniform. Combine phase B in a separate vessel and mix until uniform. Add phase B to phase A with stirring until uniform.

What is claimed is:

1. Dye-polymer complex particle wherein the complex particles are formed from the group consisting of
   (a) (i) one or more cationic polymers containing quaternary ammonium moieties and
   (a) (ii) one or more anionic dyes,
   wherein components (a) (i) and (a) (ii) are complexed to form water and solvent insoluble particles prior to addition to a personal care composition or product and wherein said complex particles remain as particles in the finished product,
   with the proviso that the cationic polymer of component (a) (i) is characterized by a weight average molecular weight ranging from 250,000 to 4 million Daltons.

2. The dye-polymer complex particles according to claim 1 wherein the anionic dyes of component (a) (ii) are selected from the group consisting of halogen-containing acid dyes, azo dyes, reactive dyes, anthraquinone dyes and natural acid dyes.

3. The dye-polymer complex particles according to claim 2 wherein the anionic dyes of component (a) (ii) are selected from the group consisting of D & C Red 21, D & C Orange 5, D & C Red 27, D & C Orange 10, D & C Red 3, D & C Red 7, D & C Red 6, D & C Red 2, D & C Red 4, D & C Red 8, D & C Red 33, D & C Yellow 5, D & C Yellow 6, D & C Green 5, D & C Yellow 10, D&C Green 3, D & C Blue 1, D & C Blue 2, D & C Violet 1, Food Black 1 (CI No. 28440), Acid Black 1 (CI No. 20470), Acid Black 2 (CI No. 50420), Food Red 10 (CI No. 18050), Food Blue 1 (CI No. 73015), Food Brown 3 (Cl No.20285), Food Red 3 (Cl No.14720), Food Red 7 (CI No. 16255), Food Yellow No.4 (CI No. 19140), Food Yellow No.13 (CI No.47005), Red No. 102, Red No. 104-1, Red No. 105-1, Red No. 106, Yellow No. 5, Red No. 227, Red No. 230-1, Orange No. 205, Yellow No. 202-1, Yellow No. 203, Green No. 204, Blue No. 205, Brown No. 201, Red No. 401, Red No. 504, Orange No. 402, Yellow No. 403-1, Yellow No. 406, Yellow No. 407, Green No. 401, Violet No. 401, Black No. 401, carminic acid and laccaic acid.

4. The dye-polymer complex particles according to claim 1 wherein the weight average molecular weight of the cationic polymer of component (a) (i) is from about 300,000 to about 2 million Daltons.

5. The dye-polymer complex particles according to claim 1 wherein the weight ratio of component (a) (i) to component (a) (ii) is from about 10,000:1 to about 1:10,000.

6. The dye-polymer complex particles according to claim 5 wherein the weight ratio of component (a) (i) to component (a) (ii) is from about 1,000:1 to about 1:1,000.

7. The dye-polymer complex particles according to claim 6 wherein the weight ratio of component (a) (i) to component (a) (ii) is from about 100:1 to about 1:100.

8. The dye-polymer complex particles according to claim 1 wherein the dye-polymer complexes of component (a) have a particle size from about 0.001 to about 500 micrometers.

9. The dye-polymer complex particles according to claim 8 wherein the dye-polymer complexes of component (a) have a particle size from about 0.01 to about 300 micrometers.

10. The dye-polymer complex particles according to claim 9 wherein the dye-polymer complexes of component (a) have a particle size from about 1 to about 300 micrometers.

11. The dye-polymer complex particles according to claim 1 wherein the cationic polymer of component (a) (i) is a reaction product of 1 to 100 weight percent of at least one cationic monomer $I_b$, 0 to 99 weight percent of one or more other copolymerizable monomers II, and optionally, 0 to 10 weight percent of a crosslinking agent.

12. The dye-polymer complex particles according to claim 11 wherein the cationic polymer of component (a) (i) in addition to containing the quaternary ammonium moieties contains groups selected from the group consisting of primary, secondary, and tertiary amines and their salts, and phosphonium salts, and mixtures thereof.

13. The dye-polymer complex particles according to claim 12 wherein the cationic polymer of component (a) (i) is obtained from homopolymerization of at least one cationic monomer $I_b$ or copolymerization of $I_b$ with a copolymerizable monomer II, wherein the cationic monomer is selected from diallyldimethyl ammonium chloride, diallyldimethyl ammonium bromide, diallyldimethyl ammonium sulfate, diallyldimethyl ammonium phosphates, dimethallyldimethyl ammonium chloride, diethylallyl dimethyl ammonium chloride, diallyl di(beta-hydroxyethyl) ammonium chloride, and diallyl di(beta-ethoxyethyl) ammonium chloride; , dimethylaminoethyl acrylate methyl chloride quaternary salt, dimethylaminoethyl acrylate methyl sulfate quaternary salt, dimethyaminoethyl acrylate benzyl chloride quaternary salt, dimethylaminoethyl methacrylate methyl chloride quaternary salt, dimethylaminoethyl methacrylate methyl sulfate quaternary salt, dimethylaminoethyl methacrylate benzyl chloride quaternary salt, diethylaminoethyl acrylate methyl chloride quaternary salt, diethylaminoethyl methacrylate methyl chloride quaternary salt, methacrylamidopropyltrimethylammonium chloride, acrylamidopropyltrimethylammonium chloride, dimethylaminopropylacrylamide methyl sulfate quaternary salt, diallyldiethylammonium chloride, diallyldimethyl ammonium chloride, 2-vinyl-N-methylpyridinium chloride and mixtures thereof.

14. The dye-polymer complex particles according to claim 1 wherein the cationic polymer of component (a) (i) in addition to containing the quaternary ammonium moieties contains groups is selected from the group consisting of reaction products of polyamidoamines and epichlorohydrin, reaction products of polyamines and epichlorohydrin, reaction products of polyamine and dicyandiamide polymers, and reaction products of epichlorohydrin and amines.

15. The dye-polymer complex particles according to claim 14 wherein the cationic polymer of component (a) (i) is linear or crosslinked.

16. The dye-polymer complex particles according to claim 14 wherein the cationic polymer of component (a) (i) is a reaction product of epichlorohydrin and dimethylamine with ethylenediamine as a crosslinking agent.

17. A personal care composition comprising
(a) an effective colorizing amount of the dye-polymer complex particles according to claim 1 and
(b) a cosmetically acceptable adjuvant.

18. The composition according to claim 17 further comprising
(c) at least one compound selected from the group consisting of the ultraviolet light absorbers, antioxidants, tocopherol, tocopherol acetate, hindered amine light stabilizers, complex formers, optical brighteners, surfactants, and polyorganosiloxanes.

19. The composition according to claim 18 where the ultraviolet light absorbers are selected from the group consisting of 2H-benzotriazoles, s-triazines, benzophenones, alpha-cyanoacrylates, oxanilides, benzoxazinones, benzoates and alpha-alkyl cinnamates.

20. The composition according to claim 17 further comprising
(d) a dye or a pigment or mixtures thereof.

21. The composition according to claim 17 wherein the dye-polymer complex of component (a) is present in a concentration of about 0.0001 weight % to about 50 weight % based on the total composition.

22. The composition according to claim 21 where the dye-polymer complex of component (a) is present in a concentration of about 0.01 weight % to about 25 weight % based on the total composition.

23. The composition according to claim 17 wherein the personal care product is selected from the group consisting of skin-care products, bath and shower products, liquid soaps, bar soaps, preparations containing fragrances and odoriferous substances, hair-care products, dentifrices, deodorizing and antiperspirant preparations, decorative preparations, light protection formulations and preparations containing active ingredients, shaving lotions, body oils, body lotions, body gels, treatment creams, skin protection ointments, shaving preparations, skin powders, shampoos, hair conditioners, 2 in 1 conditioners, leave in and rinse off conditioners, agents for styling and treating hair, hair perming agents, relaxants, hair sprays and lacquers, permanent hair dyeing systems, semi-permanent hair dyeing systems, temporary hair dyeing systems, hair bleaching agents, lipsticks, nail varnishes, eye shadows, mascaras, dry and moist make-up, rouge, powders, depilatory agents, sun care and after sun products.

* * * * *